US010500001B2

(12) United States Patent
Yu et al.

(10) Patent No.: US 10,500,001 B2
(45) Date of Patent: *Dec. 10, 2019

(54) SURGICAL ROBOTICS SYSTEM

(71) Applicant: Auris Health, Inc., Redwood City, CA (US)

(72) Inventors: Alan Yu, Union City, CA (US); Frederic H. Moll, San Francisco, CA (US); Benjamin Richter, San Leandro, CA (US); Mark H. Olson, San Carlos, CA (US); Jason Gonzalez, San Francisco, CA (US); Kyle Andrew Tucker, San Francisco, CA (US); Paxton Maeder-York, San Francisco, CA (US); Gregory T. Schulte, Oakland, CA (US)

(73) Assignee: Auris Health, Inc., Redwood City, CA (US)

( * ) Notice: Subject to any disclaimer, the term of this patent is extended or adjusted under 35 U.S.C. 154(b) by 260 days.

This patent is subject to a terminal disclaimer.

(21) Appl. No.: 15/453,798

(22) Filed: Mar. 8, 2017

(65) Prior Publication Data

US 2017/0172673 A1 Jun. 22, 2017

Related U.S. Application Data

(63) Continuation of application No. 15/154,762, filed on May 13, 2016, now Pat. No. 9,622,827.
(Continued)

(51) Int. Cl.
*A61B 34/30* (2016.01)
*A61B 34/35* (2016.01)
(Continued)

(52) U.S. Cl.
CPC .......... *A61B 34/30* (2016.02); *A61B 1/00149* (2013.01); *A61B 34/35* (2016.02);
(Continued)

(58) Field of Classification Search
CPC ......... A61B 34/30; A61B 34/35; A61B 34/70; A61B 2034/301; A61B 2034/302;
(Continued)

(56) References Cited

U.S. PATENT DOCUMENTS 4,878,494 A  11/1989  Phillips et al.
5,013,018 A  5/1991   Sicek
(Continued)

FOREIGN PATENT DOCUMENTS

JP  2012-005557   1/2012
KR  101448201    10/2014
(Continued)

OTHER PUBLICATIONS

PCT Invitation to Pay Additional Fees, PCT Application No. PCT/US16/32505, dated Jul. 19, 2016, 2 pp.
(Continued)

*Primary Examiner* — Tuan V Nguyen
(74) *Attorney, Agent, or Firm* — Knobbe, Martens Olson & Bear LLP

(57) ABSTRACT

A surgical robotics system with robotic arms is configurable to perform a variety of surgical procedures. The surgical robotics system includes a table, column, base, and robotic arms that are either column-mounted, rail-mounted, or mounted on a separate unit. In a column-mounted configuration, the column includes column rings that translate vertically and rotate about the column. The robotic arms are attached to the column rings. In a rail-mounted configuration, the base includes base rails that translate along the base. The robotic arms are attached to the base rails. In both
(Continued)

configurations, the robotic arms move independently from each other and include a multiple arm segments. Each arm segment provides an additional degree of freedom to the robotic arm. Thus, the surgical robotics system may position the robotic arms into numerous configurations to access different parts of a patient's body.

30 Claims, 30 Drawing Sheets

Related U.S. Application Data

(60) Provisional application No. 62/162,486, filed on May 15, 2015, provisional application No. 62/162,467, filed on May 15, 2015, provisional application No. 62/193,604, filed on Jul. 17, 2015, provisional application No. 62/201,518, filed on Aug. 5, 2015, provisional application No. 62/203,530, filed on Aug. 11, 2015, provisional application No. 62/235,394, filed on Sep. 30, 2015.

(51) Int. Cl.
| | |
|---|---|
| *A61B 34/00* | (2016.01) |
| *A61G 7/005* | (2006.01) |
| *A61G 7/008* | (2006.01) |
| *A61G 7/015* | (2006.01) |
| *A61G 7/075* | (2006.01) |
| *A61G 13/02* | (2006.01) |
| *A61B 1/00* | (2006.01) |
| *A61G 13/04* | (2006.01) |
| *A61G 13/06* | (2006.01) |
| *A61G 13/08* | (2006.01) |
| *A61G 13/10* | (2006.01) |
| *A61G 13/12* | (2006.01) |

(52) U.S. Cl.
CPC .............. *A61B 34/70* (2016.02); *A61G 7/005* (2013.01); *A61G 7/008* (2013.01); *A61G 7/015* (2013.01); *A61G 7/0755* (2013.01); *A61G 13/02* (2013.01); *A61G 13/04* (2013.01); *A61G 13/06* (2013.01); *A61G 13/08* (2013.01); *A61G 13/102* (2013.01); *A61G 13/1245* (2013.01); *A61B 2034/301* (2016.02); *A61B 2034/302* (2016.02); *Y10S 901/02* (2013.01); *Y10S 901/27* (2013.01); *Y10S 901/28* (2013.01)

(58) Field of Classification Search
CPC ........ A61B 2034/303; A61B 2034/304; A61B 2034/305; A61B 2034/306
See application file for complete search history.

(56) References Cited

U.S. PATENT DOCUMENTS

| | | | |
|---|---|---|---|
| 5,160,106 | A | 11/1992 | Monick |
| 5,555,897 | A | 9/1996 | Lathrop, Jr. et al. |
| 5,571,072 | A | 11/1996 | Kronner |
| 5,762,458 | A | 6/1998 | Wang et al. |
| 5,814,038 | A | 9/1998 | Jensen et al. |
| 5,926,875 | A | 7/1999 | Okamoto et al. |
| 5,944,476 | A | 8/1999 | Bacchi et al. |
| 6,170,102 | B1 | 1/2001 | Kreuzer |
| 6,202,230 | B1 | 3/2001 | Borders |
| 6,620,174 | B2 | 9/2003 | Jensen et al. |
| 6,676,669 | B2 | 1/2004 | Charles et al. |
| 6,804,581 | B2 | 10/2004 | Wang |
| 7,025,761 | B2 | 4/2006 | Wang et al. |
| 7,074,179 | B2 | 7/2006 | Wang et al. |
| 7,607,440 | B2 | 10/2009 | Coste-Maniere et al. |
| 7,695,481 | B2 | 4/2010 | Wang et al. |
| 7,763,015 | B2 | 7/2010 | Cooper et al. |
| 7,789,874 | B2 | 9/2010 | Yu et al. |
| 7,850,642 | B2 | 12/2010 | Moll et al. |
| 7,963,288 | B2 | 6/2011 | Rosenberg et al. |
| 7,972,298 | B2 | 7/2011 | Wallace et al. |
| 7,974,681 | B2 | 7/2011 | Wallace et al. |
| 7,976,539 | B2 | 7/2011 | Hlavka et al. |
| 7,979,157 | B2 | 7/2011 | Anvari |
| 7,996,110 | B2 | 8/2011 | Lipow et al. |
| 8,005,537 | B2 | 8/2011 | Hlavka et al. |
| 8,021,326 | B2 | 9/2011 | Moll et al. |
| 8,052,636 | B2 | 11/2011 | Moll et al. |
| 8,108,069 | B2 | 1/2012 | Stahler et al. |
| 8,142,420 | B2 | 3/2012 | Schena |
| 8,146,874 | B2 | 4/2012 | Yu |
| 8,172,747 | B2 | 5/2012 | Wallace et al. |
| 8,190,238 | B2 | 5/2012 | Moll et al. |
| 8,230,863 | B2 | 7/2012 | Ravikumar et al. |
| 8,257,303 | B2 | 9/2012 | Moll et al. |
| 8,311,626 | B2 | 11/2012 | Hlavka et al. |
| 8,343,096 | B2 | 1/2013 | Kirschenman et al. |
| 8,348,931 | B2 | 1/2013 | Cooper et al. |
| 8,394,054 | B2 | 3/2013 | Wallace et al. |
| 8,400,094 | B2 | 3/2013 | Schena |
| 8,409,136 | B2 | 4/2013 | Wallace et al. |
| 8,409,172 | B2 | 4/2013 | Moll et al. |
| 8,414,598 | B2 | 4/2013 | Brock et al. |
| 8,425,404 | B2 | 4/2013 | Wilson et al. |
| 8,469,945 | B2 | 6/2013 | Schena |
| 8,498,691 | B2 | 7/2013 | Moll et al. |
| 8,506,556 | B2 | 8/2013 | Schena |
| 8,512,353 | B2 | 8/2013 | Rosielle et al. |
| 8,515,576 | B2 | 8/2013 | Lipow et al. |
| 8,617,102 | B2 | 12/2013 | Moll et al. |
| 8,641,698 | B2 | 2/2014 | Sanchez et al. |
| 8,801,661 | B2 | 8/2014 | Moll et al. |
| 8,911,429 | B2 | 12/2014 | Olds et al. |
| 8,926,603 | B2 | 1/2015 | Hlavka et al. |
| 8,960,622 | B2 | 2/2015 | von Pechmann et al. |
| 8,968,333 | B2 | 3/2015 | Yu et al. |
| 8,974,408 | B2 | 3/2015 | Wallace et al. |
| 9,023,060 | B2 | 5/2015 | Cooper et al. |
| 9,259,281 | B2 | 2/2016 | Griffiths et al. |
| 9,314,306 | B2 | 4/2016 | Yu |
| 9,326,822 | B2 | 5/2016 | Lewis et al. |
| 9,358,076 | B2 | 6/2016 | Moll et al. |
| 9,408,669 | B2 | 8/2016 | Kokish et al. |
| 9,452,018 | B2 | 9/2016 | Yu |
| 9,457,168 | B2 | 10/2016 | Moll et al. |
| 9,504,604 | B2 | 11/2016 | Alvarez |
| 9,554,865 | B2 | 1/2017 | Olds et al. |
| 9,561,083 | B2 | 2/2017 | Yu et al. |
| 9,566,201 | B2 | 2/2017 | Yu |
| 9,615,889 | B2 | 4/2017 | Jensen |
| 9,622,827 | B2 | 4/2017 | Yu et al. |
| 9,629,682 | B2 | 4/2017 | Wallace et al. |
| 9,636,184 | B2 | 5/2017 | Lee et al. |
| 9,713,499 | B2 | 7/2017 | Bar et al. |
| 9,713,509 | B2 | 7/2017 | Schuh et al. |
| 9,727,963 | B2 | 8/2017 | Mintz et al. |
| 9,737,371 | B2 | 8/2017 | Romo et al. |
| 9,737,373 | B2 | 8/2017 | Schuh |
| 9,744,335 | B2 | 8/2017 | Jiang |
| 9,763,741 | B2 | 9/2017 | Alvarez et al. |
| 9,788,910 | B2 | 10/2017 | Schuh |
| 9,795,454 | B2 | 10/2017 | Seeber et al. |
| 9,818,681 | B2 | 11/2017 | Machida |
| 9,820,819 | B2 | 11/2017 | Olson |
| 9,844,412 | B2 | 12/2017 | Bogusky et al. |
| 9,850,924 | B2 | 12/2017 | Vogtherr et al. |
| 9,867,635 | B2 | 1/2018 | Alvarez et al. |
| 9,907,458 | B2 | 3/2018 | Schena |
| 9,918,681 | B2 | 3/2018 | Wallace et al. |
| 9,999,476 | B2 | 6/2018 | Griffiths et al. |
| 10,016,900 | B1 | 7/2018 | Meyer et al. |
| 10,022,192 | B1 | 7/2018 | Ummalaneni |
| 10,136,959 | B2 | 11/2018 | Mintz et al. |

(56) References Cited

U.S. PATENT DOCUMENTS

| | | |
|---|---|---|
| 10,145,747 B1 | 12/2018 | Lin et al. |
| 10,159,532 B1 | 12/2018 | Ummalaneni et al. |
| 10,231,793 B2 | 3/2019 | Romo |
| 10,244,926 B2 | 4/2019 | Noonan et al. |
| 2002/0162926 A1 | 11/2002 | Nguyen |
| 2002/0165524 A1 | 11/2002 | Sanchez et al. |
| 2002/0170116 A1 | 11/2002 | Borders |
| 2003/0191455 A1 | 10/2003 | Sanchez et al. |
| 2004/0243147 A1 | 12/2004 | Lipow |
| 2004/0261179 A1 | 12/2004 | Blumenkranz |
| 2005/0222554 A1* | 10/2005 | Wallace .......... A61B 5/042 606/1 |
| 2006/0069383 A1 | 3/2006 | Bogaerts |
| 2006/0200026 A1 | 9/2006 | Wallace et al. |
| 2008/0027464 A1 | 1/2008 | Moll et al. |
| 2008/0039867 A1 | 2/2008 | Feussner |
| 2008/0082109 A1 | 4/2008 | Moll et al. |
| 2008/0167750 A1 | 7/2008 | Stahler |
| 2008/0195081 A1 | 8/2008 | Moll et al. |
| 2008/0218770 A1 | 9/2008 | Moll et al. |
| 2009/0036900 A1 | 2/2009 | Moll |
| 2009/0062602 A1 | 3/2009 | Rosenberg et al. |
| 2010/0185211 A1 | 7/2010 | Herman |
| 2010/0204713 A1 | 8/2010 | Ruiz |
| 2010/0286712 A1 | 11/2010 | Won et al. |
| 2010/0308195 A1* | 12/2010 | Yu .......... A61B 90/50 248/349.1 |
| 2011/0238083 A1 | 9/2011 | Moll et al. |
| 2011/0270273 A1 | 11/2011 | Moll et al. |
| 2012/0136372 A1 | 5/2012 | Amat Girbau et al. |
| 2012/0191079 A1 | 7/2012 | Moll et al. |
| 2012/0191083 A1 | 7/2012 | Moll et al. |
| 2012/0191086 A1 | 7/2012 | Moll et al. |
| 2012/0253332 A1 | 10/2012 | Moll |
| 2012/0266379 A1 | 10/2012 | Hushek |
| 2012/0296161 A1 | 11/2012 | Wallace et al. |
| 2013/0190741 A1 | 7/2013 | Moll et al. |
| 2013/0255425 A1 | 10/2013 | Schena |
| 2013/0338679 A1 | 12/2013 | Rosielle et al. |
| 2014/0142591 A1 | 5/2014 | Alvarez et al. |
| 2014/0180309 A1 | 6/2014 | Seeber et al. |
| 2014/0188132 A1 | 7/2014 | Kang |
| 2014/0249546 A1 | 9/2014 | Shvartsberg et al. |
| 2014/0309649 A1 | 10/2014 | Alvarez et al. |
| 2014/0316436 A1 | 10/2014 | Bar et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0038981 A1 | 2/2015 | Kilroy et al. |
| 2015/0051592 A1 | 2/2015 | Kintz |
| 2015/0101442 A1 | 4/2015 | Romo |
| 2015/0119638 A1 | 4/2015 | Yu et al. |
| 2015/0164594 A1 | 6/2015 | Romo et al. |
| 2015/0164596 A1 | 6/2015 | Romo |
| 2015/0335389 A1 | 11/2015 | Greenberg |
| 2015/0335480 A1 | 11/2015 | Alvarez et al. |
| 2016/0001038 A1 | 1/2016 | Romo et al. |
| 2016/0157942 A1* | 6/2016 | Gombert .......... B25J 9/1666 606/130 |
| 2016/0270865 A1 | 9/2016 | Landey et al. |
| 2016/0279394 A1 | 9/2016 | Moll et al. |
| 2016/0287279 A1 | 10/2016 | Bovay et al. |
| 2016/0296294 A1 | 10/2016 | Moll et al. |
| 2016/0346052 A1 | 12/2016 | Rosielle et al. |
| 2016/0374541 A1 | 12/2016 | Agrawal et al. |
| 2017/0007337 A1 | 1/2017 | Dan |
| 2017/0065364 A1 | 3/2017 | Schuh et al. |
| 2017/0065365 A1 | 3/2017 | Schuh |
| 2017/0071692 A1 | 3/2017 | Taylor et al. |
| 2017/0071693 A1 | 3/2017 | Taylor et al. |
| 2017/0086929 A1 | 3/2017 | Moll et al. |
| 2017/0100199 A1 | 4/2017 | Yu et al. |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0135771 A1 | 5/2017 | Auld et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209217 A1 | 7/2017 | Jensen |
| 2017/0215976 A1 | 8/2017 | Nowlin et al. |
| 2017/0215978 A1 | 8/2017 | Wallace et al. |
| 2017/0290631 A1 | 10/2017 | Lee et al. |
| 2017/0304021 A1 | 10/2017 | Hathaway |
| 2017/0325906 A1 | 11/2017 | Piecuch et al. |
| 2017/0333679 A1 | 11/2017 | Jiang |
| 2017/0340353 A1 | 11/2017 | Ahluwalia et al. |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0055583 A1 | 3/2018 | Schuh et al. |
| 2018/0078439 A1 | 3/2018 | Cagle et al. |
| 2018/0078440 A1 | 3/2018 | Koenig et al. |
| 2018/0079090 A1 | 3/2018 | Koenig et al. |
| 2018/0177556 A1 | 6/2018 | Noonan et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |

FOREIGN PATENT DOCUMENTS

| | | |
|---|---|---|
| WO | WO 10/068005 | 6/2010 |
| WO | WO 15/010788 | 1/2015 |

OTHER PUBLICATIONS

PCT International Search Report and Written Opinion, PCT Application No. PCT/US16/32505, dated Sep. 23, 2016, 15 pp.

United States Office Action, U.S. Appl. No. 15/154,762, dated Oct. 18, 2016, 7 pp.

* cited by examiner

SURGICAL ROBOTICS SYSTEM

CROSS-REFERENCE TO RELATED APPLICATIONS

This application is a continuation of prior, U.S. application Ser. No. 15/154,762, filed on May 13, 2016, now issued as U.S. Patent No. 9,622,827, which claims the benefit of and priority to U.S. Provisional Application No. 62/162,486 filed May 15, 2015, U.S. Provisional Application No. 62/162,467 filed May 15, 2015, U.S. Provisional Application No. 62/193,604 filed Jul. 17, 2015, U.S. Provisional Application No. 62/201,518 filed Aug. 5, 2015, U.S. Provisional Application No. 62/203,530 filed Aug. 11, 2015, and U.S. Provisional Application No. 62/235,394 filed Sep. 30, 2015, which are each incorporated by reference herein in its entirety. This application relates to virtual rails that may be incorporated into a surgical robotics system, such as those disclosed in U.S. application Ser. No. 14/871,253, which is incorporated by reference herein in its entirety.

BACKGROUND

1. Field of Art

This description generally relates to surgical robotics, and particularly to a robotics system configurable for a variety of surgical procedures.

2. Description of the Related Art

Robotic technologies have a range of applications. In particular, robotic arms help complete tasks that a human would normally perform. For example, factories use robotic arms to manufacture automobiles and consumer electronics products. Additionally, scientific facilities use robotic arms to automate laboratory procedures such as transporting microplates. Recently, physicians have started using robotic arms to help perform surgical procedures. For instance, physicians use robotic arms to control surgical instruments inside a patient. However, existing medical systems including robotic arms have a high capital cost and are typically specialized to perform limited types of surgical procedures. Thus, physicians or their assistants may need to obtain multiple robotic arm systems to accommodate a range of surgical procedures. Manually reconfiguring a robotic arm system for each surgical procedure is also time-consuming and physically demanding for the physicians.

SUMMARY

A surgical robotics system with robotic arms is configurable to perform a variety of surgical procedures. The surgical robotics system includes a table, column, base, and robotic arms that are either column-mounted, rail-mounted, or mounted on a separate unit (e.g., a free-standing column). In a column-mounted configuration, the column includes column rings that translate vertically and rotate about the column. The robotic arms are attached to the column rings. In a rail-mounted configuration, the base includes base rails that translate along the base. The robotic arms are attached to the base rails. In both configurations, the robotic arms move independently from each other and include a multiple arm segments. Each arm segment provides an additional degree of freedom to the robotic arm. Thus, the surgical robotics system may position the robotic arms into numerous configurations to access different parts of a patient's body. For example, the robotic arms access the lower area of the body for ureteroscopy, the core (abdomen) area of the body for prostatectomy, and the upper area of the body for bronchoscopy. The configurability of the robotic arms is an advantage because physicians may use the same surgical robotics system to perform a wide range of surgical procedures.

The surgical robotics system includes several features that provide additional advantages. For example, the table includes a swivel segment that rotates laterally using double curved rails or a swivel mechanism with bearings. Rotating a patient on the table laterally provides the robotic arms—or a physician—greater access to operate on the patient. Further, the double curved rails enable the table to support high cantilever loads of the patient's weight in a rotated position. In another example, the robotic arms are configurable into a compact stowed position and stored inside the base. The base protects stored robotic arms from contamination or de-sterilization when not in use.

Reference will now be made in detail to several embodiments, examples of which are illustrated in the accompanying figures. It is noted that wherever practicable similar or like reference numbers may be used in the figures and may indicate similar or like functionality. The figures depict embodiments of the described system (or method) for purposes of illustration only. One skilled in the art will readily recognize from the following description that alternative embodiments of the structures and methods illustrated herein may be employed without departing from the principles described herein.

DETAILED DESCRIPTION

I. System Overview

Figure 1:
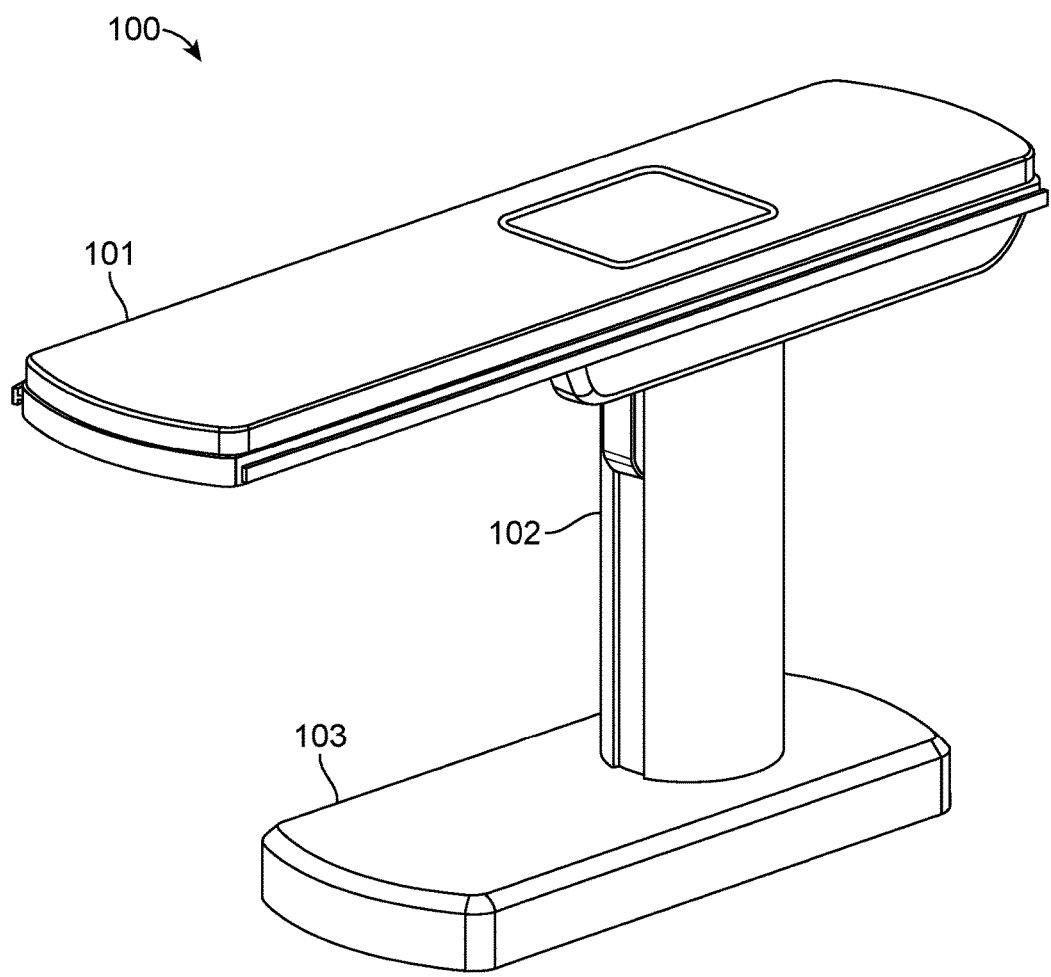
FIG. 1 is an isometric view of a surgical robotics system according to an embodiment.

FIG. 1 is an isometric view of a surgical robotics system 100 according to an embodiment. A user, e.g., a physician or assistant, uses the surgical robotics system 100 to perform robotically-assisted surgery on a patient. The surgical robotics system 100 includes a table 101, column 102, and base 103 physically coupled together. Although not shown in FIG. 1, the table 101, column 102, and/or base 103 may house, connect to, or use electronics, fluidics, pneumatics, aspiration, or other electrical and mechanical components that support the function of the surgical robotics system 100.

The table 101 provides support for a patient undergoing surgery using the surgical robotics system 100. Generally, the table 101 is parallel to the ground, though the table 101 may change its orientation and configuration to facilitate a variety of surgical procedures. The table 101 is further described with reference to FIGS. 2A-I in Section II. Table.

The column 102 is coupled to the table 101 on one end and coupled to the base 103 on the other end. Generally, the column 102 is cylindrically shaped to accommodate column rings coupled to the column 102, which are further described with reference to FIGS. 5A-E in Section V. Column Ring, however the column 102 may have other shapes such as oval or rectangular. The column 102 is further described with reference to FIGS. 3A-B in Section III. Column.

The base 103 is parallel to the ground and provides support for the column 102 and the table 101. The base 103 may include wheels, treads, or other means of positioning or transporting the surgical robotics system 100. The base 103 is further described with reference to FIGS. 8A-E in Section VIII. Base.

Alternative views and embodiments of the surgical robotics system 100 including the above mentioned components are further illustrated and described at least in U.S. Provisional Application No. 62/162,486 filed May 15, 2015 and U.S. Provisional Application No. 62/162,467 filed May 15, 2015.

II. Table

Figure 2A:
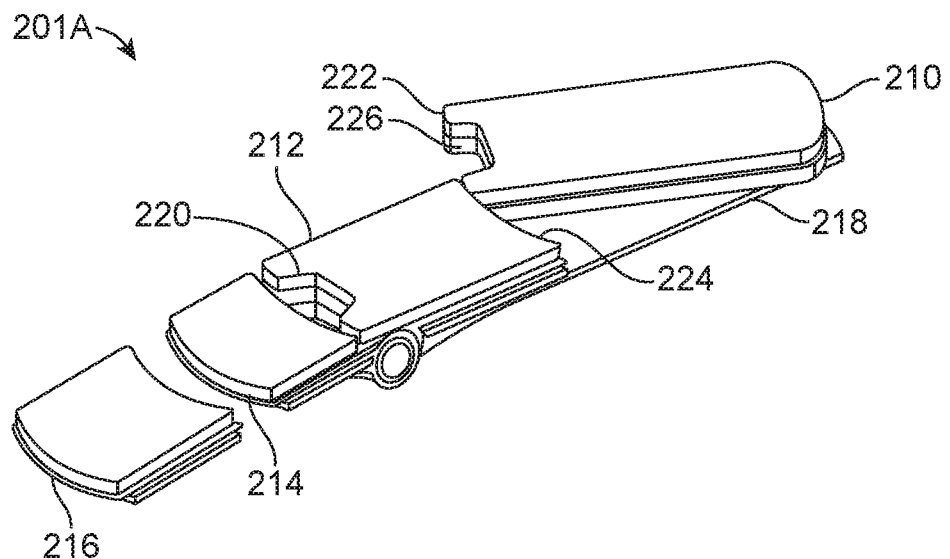
FIG. 2A is an isometric view of a table of the surgical robotics system according to one embodiment.

FIG. 2A is an isometric view of a table 201A of the surgical robotics system 100 according to one embodiment. The table 201A is an embodiment of the table 101 in FIG. 1. The table 201A includes a set of one or more segments. Generally, a user changes the configuration of the table 201A by configuring the set of segments. The surgical robotics system 100 may also configure the segments automatically, for example, by using a motor to reposition a segment of the set of segments. An example set of segments is shown in FIG. 2A, and includes a swivel segment 210, center segment 212, foldable segment 214, detachable segment 216, and table base 218. The swivel segment 210, center segment 212, and foldable segment 214 are coupled to the table base 218. FIG. 2A shows the detachable segment 216 separated from the table base 218, though the detachable segment 216 may also be coupled to the table base 218. In various implementations, additional or fewer segments may be used.

An advantage of configuring the set of segments of the table 201A is that a configured table 201A may provide greater access to a patient on the table 201A. For instance, the surgical robotics system 100 performs a surgical procedure on the patient that requires access to the groin area of the patient. When a patient is laying face-up on a typical surgical bed, there is more access to the patient's head, arms, and legs than to the patient's groin area. Since the groin area is located toward the center of the patient's body, the legs often obstruct access to the groin area. The detachable segment 216 is detachable from the table 201A. The table 201A without the detachable segment 216 provides greater access to the groin area of a patient lying on the table 201A with the patient's head toward the side of the table 201A with the swivel segment 210. In particular, removing the detachable segment 216 opens more space, for example, to insert a surgical instrument into the groin area. If additional space is required to access the groin area, the foldable segment 214 may be folded down, away from the patient (further described in FIG. 2H). The center segment 212 includes a cutout section 220, which also provides greater access to the groin area.

The swivel segment 210 pivots laterally relative to the table 201A. The swivel segment 210 includes an arcuate edge 222 and the center segment 212 also includes in arcuate edge 224. Due to the arcuate edges, there is minimal gap between the swivel segment 210 and the center segment 212 as the swivel segment 210 pivots away from or toward the table 201A. A configuration of the table 201A with the swivel segment 210 pivoted away from the table 201A provides greater access to the groin area because the other segments of the table 201A are not obstructing the groin area. An example of this configuration is further described with respect to FIGS. 7C-D in Section VII. A. Lower Body Surgery. Additionally, the swivel segment 210 also includes a cutout section 226, which provides yet greater access to the groin area.

Figure 2B:
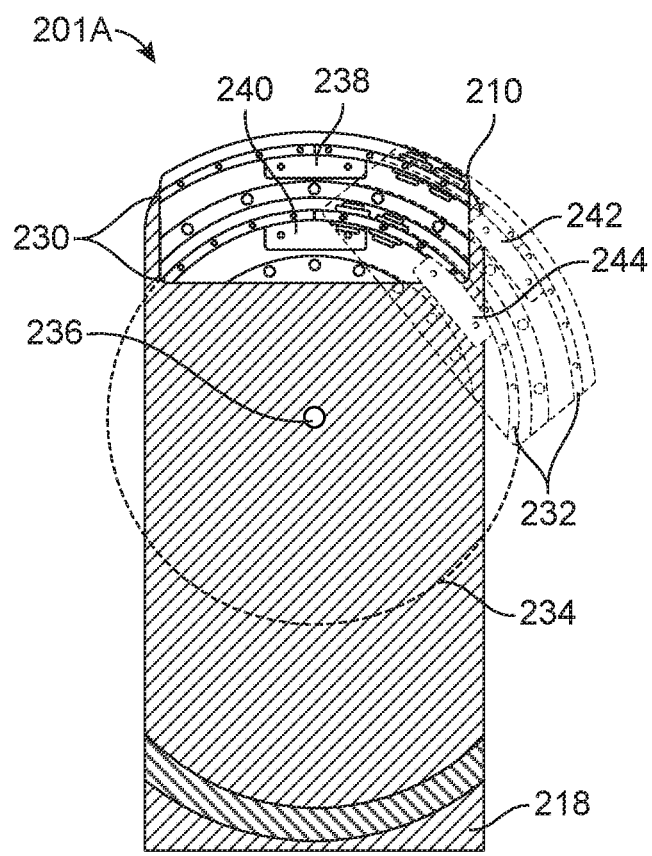
FIG. 2B is a top view of the table according to one embodiment.

FIG. 2B is a top view of the table 201A according to one embodiment. Specifically, FIG. 2B shows the table base 218 with a partial cutaway view and a portion of the swivel segment 210. Components inside the swivel segment 210 are exposed for purposes of illustration. The table base 218 includes double curved rails 230, that is, two curved linear rails (also referred to as a first bearing subassembly). The swivel segment 210 also includes double curved rails 232 (also referred to as a second bearing subassembly). The first bearing assembly coupled to the second bearing assembly may be referred to as a bearing mechanism. The double curved rails 230 of the table base 218 engage with the double curved rails 232 of the swivel segment 210. Both double curved rails are concentric to a virtual circle 234. The swivel segment 210 pivots about an axis passing through a point 236 at the center of the virtual circle 234 perpendicular to the plane of the table base 218. The double curved rails 230 of the table base 218 include a first carriage 238 and a second carriage 240. Similarly, the double curved rails 232 of the swivel segment 210 include a first carriage 242 and a second carriage 244. The carriages provide structural support and negate moment loads, which enables the double curved rails to support high cantilevered loads up to at least 500 pounds. For instance, pivoting a patient away from the table 201A generates a high cantilevered load on the double curved rails supporting the patient's weight. The table base 218 and swivel segment 210 may include additional load-sharing components such as rollers, cam followers, and bearings. In some embodiments, the swivel segment 210 and table base 218 each include a single curved rail instead of double curved rails. Further, each curved rail may include additional or fewer carriages.

Figure 2C:
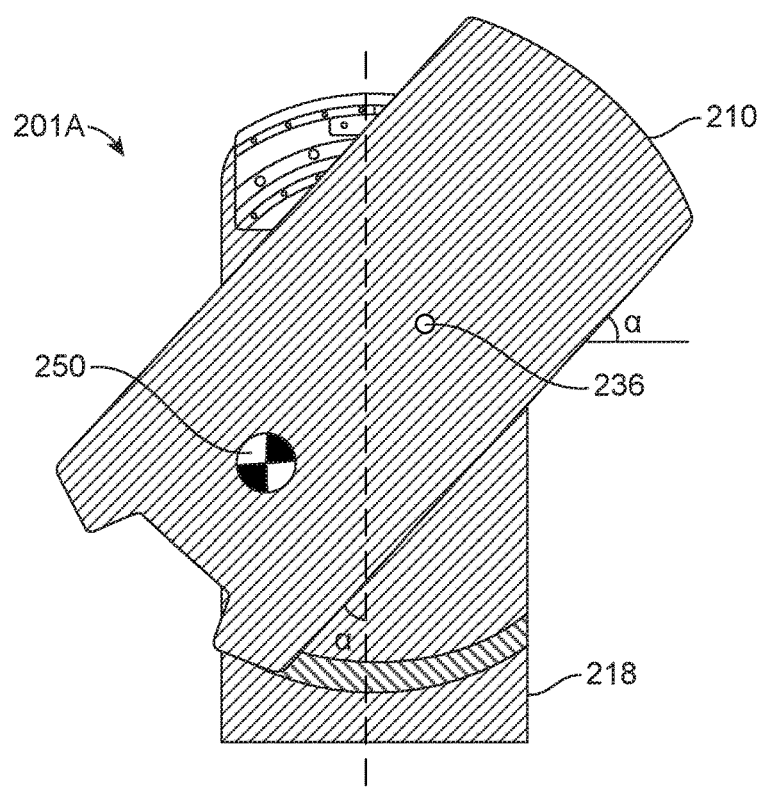
FIG. 2C is a top view of a swivel segment of a table according to one embodiment.
Figure 2D:
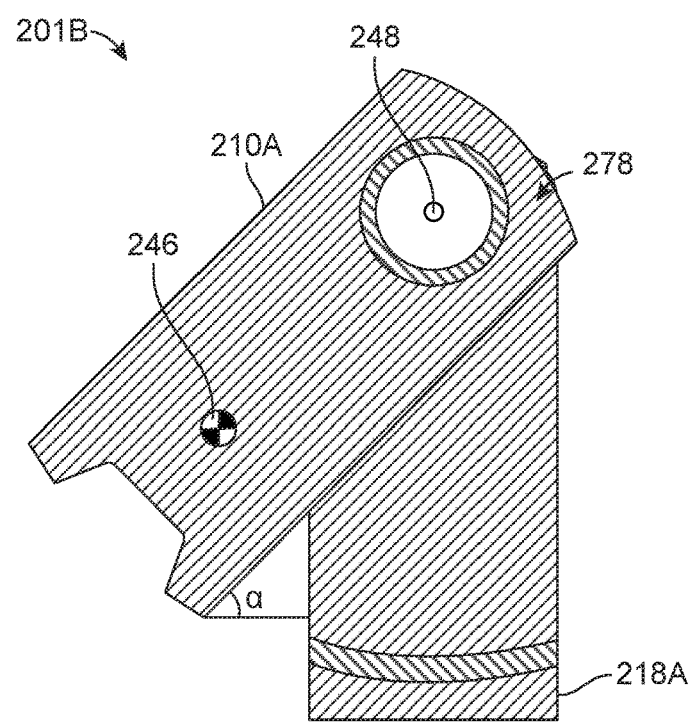
FIG. 2D is a top view of a swivel segment of the table according to one embodiment.

FIG. 2C is a top view of the swivel segment 210 of the table 201A according to one embodiment. The center of mass 250 illustrates the center of mass of the swivel segment 210 and a patient (not shown) lying on the swivel segment 210. The swivel segment 210 is pivoted at an angle α about the axis 236. Compared to the center of mass 246 shown in FIG. 2D, the center of mass 250 is closer toward the table base 218 (corresponding to table base 218B in FIG. 2D), even though the swivel segments in both FIG. 2C and FIG. 2D are each pivoted at the same angle α. Keeping the center of mass 250 close toward the table 218 helps the swivel segment 210 support greater cantilever loads—due to the patient—without tipping over the surgical robotics system. In some embodiments, the swivel segment 210 may be rotated up to an a angle of 30 degrees or 45 degrees relative to table base 218, while keeping the center of mass of the swivel segment 210 above the table 201A.

FIG. 2D is a top view of a swivel segment 210A of a table 201B according to one embodiment. Specifically, the table 201B includes a table base 218A and a swivel segment 210A. The table 201B does not include double curved rails, but instead includes a swivel mechanism 278 that is further described below with reference to FIGS. 2E-G. The center of mass 246 illustrates the center of mass of the swivel segment 210A and a patient (not shown) lying on the swivel segment 210A. The swivel segment 210A is pivoted at an angle α about an axis 248. Accordingly, the center of mass 246 is positioned off of the table base 218A.

Figure 2E:
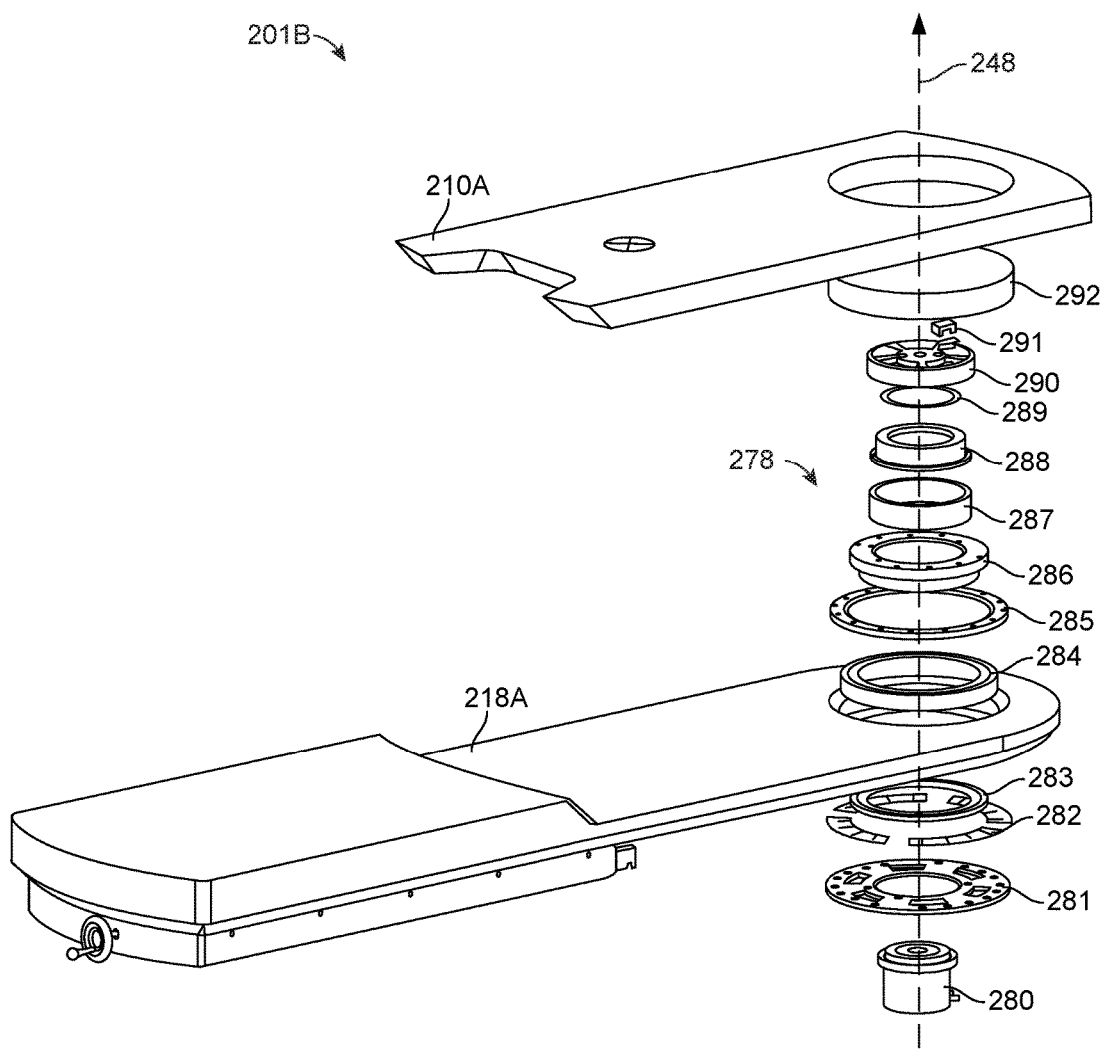
FIG. 2E is an isometric exploded view of components of a swivel mechanism according to one embodiment.

FIG. 2E is an isometric exploded view of components of a swivel mechanism 278 (which can also be referred to as a bearing mechanism) of the table 201B according to one embodiment. The swivel mechanism 278 includes a first bearing subassembly coupled to a second bearing subassembly. In particular, the swivel mechanism 278 includes a harmonic drive motor 280, static plate 281, shim 282, inner bearing race 283, bearing 284, outer bearing race cleat 285, inner bearing race support 286, static ring 287, motor housing mount 288, encoder strip 289, drive plate 290, encoder sensor 291, and swivel insert 292. The motor housing mount 288 is stationary relative to the table base 218A. The harmonic drive motor 280 rotates the swivel segment 210A about the axis 248. The first bearing subassembly includes the components described above that are coupled to the table base 218A. The second bearing subassembly includes the components described above that are coupled to the swivel segment 210A.

Figure 2F:
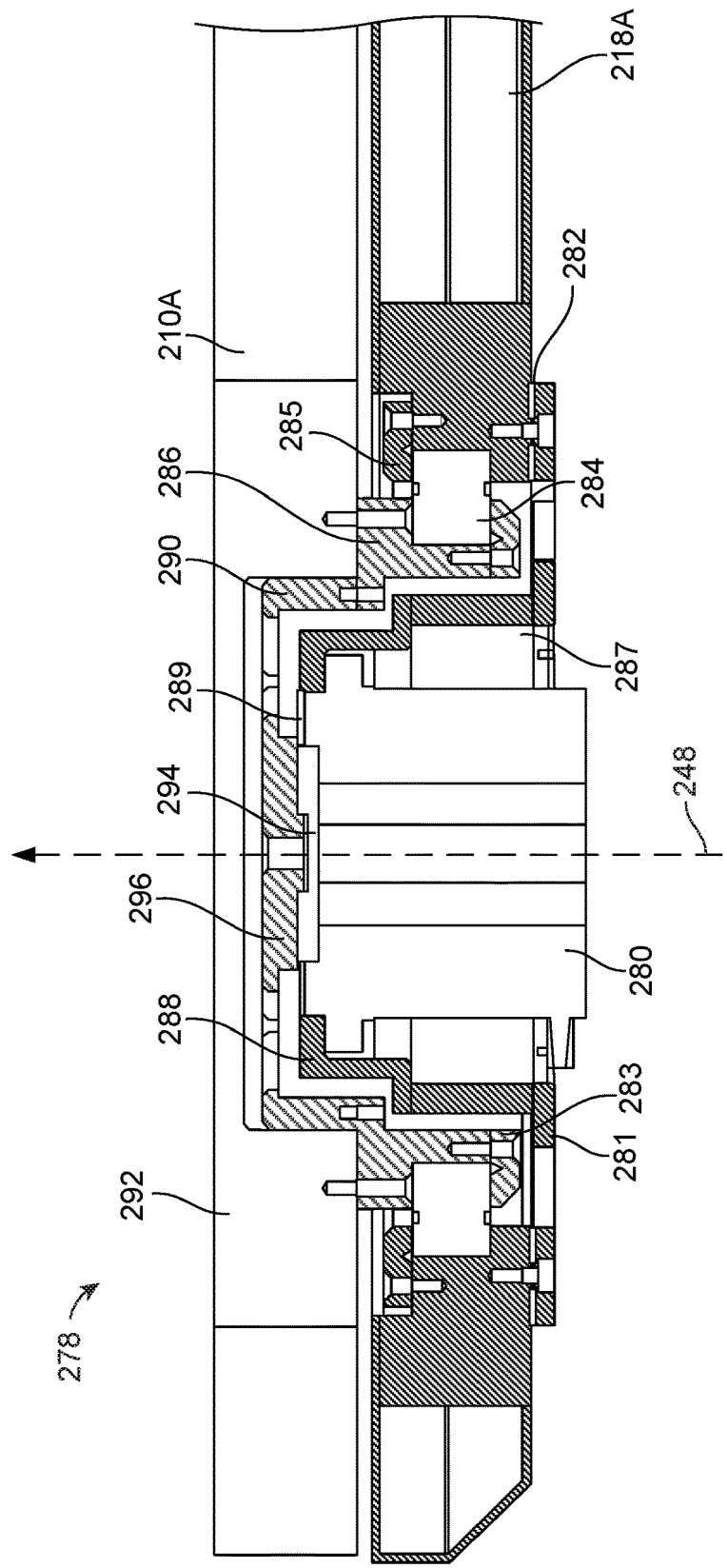
FIG. 2F is a cross sectional view of the swivel mechanism shown in FIG. 2E according to one embodiment.

FIG. 2F is a cross sectional view of the swivel mechanism 278 shown in FIG. 2E according to one embodiment. The harmonic drive motor 280 is coupled to the motor housing mount 288. The motor housing mount 288 is coupled to the static ring 287 and the static plate 281. The static plate 281 is coupled to the table base 218A using the shim 282 such that the harmonic drive motor 280 is also stationary relative to the table base 218A.

The harmonic drive motor 280 includes a driving axle 294 coupled to a driving face 296 such that the driving axle 294 and driving face 296 rotate together. The driving face 296 is coupled to the drive plate 290. The drive plate 290 is coupled to the inner bearing race support 286. The inner bearing race support 286 is coupled to the swivel insert 292 and the inner bearing race cleat 283. The inner bearing race support 286 is movably coupled to the table base 218A by the bearing 284 (e.g., a cross roller bearing). The swivel insert 292 is coupled to the swivel segment 210A such that rotating the driving axle 294 and driving face 296 causes the swivel segment 210A to rotate in the same direction. Though not shown in FIG. 2F, the swivel mechanism 278 may include additional components between the static plate 281 and the inner bearing race cleat 283 to provide additional stability, e.g., in the form of a physical hard stop. Further, though not shown in FIG. 2F, the encoder sensor 291 is coupled to the motor housing mount 288 by the encoder strip 289. The encoder sensor 291 records information about the rotation of the swivel segment 210A, e.g., the position of the swivel segment 210A up to an accuracy of 0.1 degrees at 0.01 degree resolution. FIG. 2F shows several screws (or bolts) that are used to couple components of the swivel mechanism, though it should be noted that the components may be coupled using other methods, e.g., welding, press fit, gluing, etc.

The swivel mechanism 278 allows the harmonic drive motor 280 to rotate the swivel segment 210A with precise control, while supporting a load of up to 500 pounds, e.g., from a patient lying on the swivel segment 210A. In particular, the harmonic drive motor 280 may rotate the swivel segment 210A up to a rotational velocity of 10 degrees per second, and up to 45 degrees in either direction about the axis 248. Further, the swivel segment 210A is rotated such that the maximum velocity of the center of mass of the patient is 100 millimeters per second, and the time to the maximum velocity is 0.5 seconds. In some embodiments, one of the bearings of the swivel mechanism is a cross roller bearing—e.g., with ball bearings with a bearing friction coefficient of approximately 0.0025—that helps further provide stability to allow the precise rotation of the swivel segment 210A, while maintaining cantilever loads from the patient's weight. The harmonic drive motor 280 can generate up to 33 Newton meters of torque to rotate the swivel segment 210A with the weight of the patient. In some embodiments, the harmonic drive motor 280 includes an internal brake with a holding torque of at least 40 Newton meters.

Figure 2G:
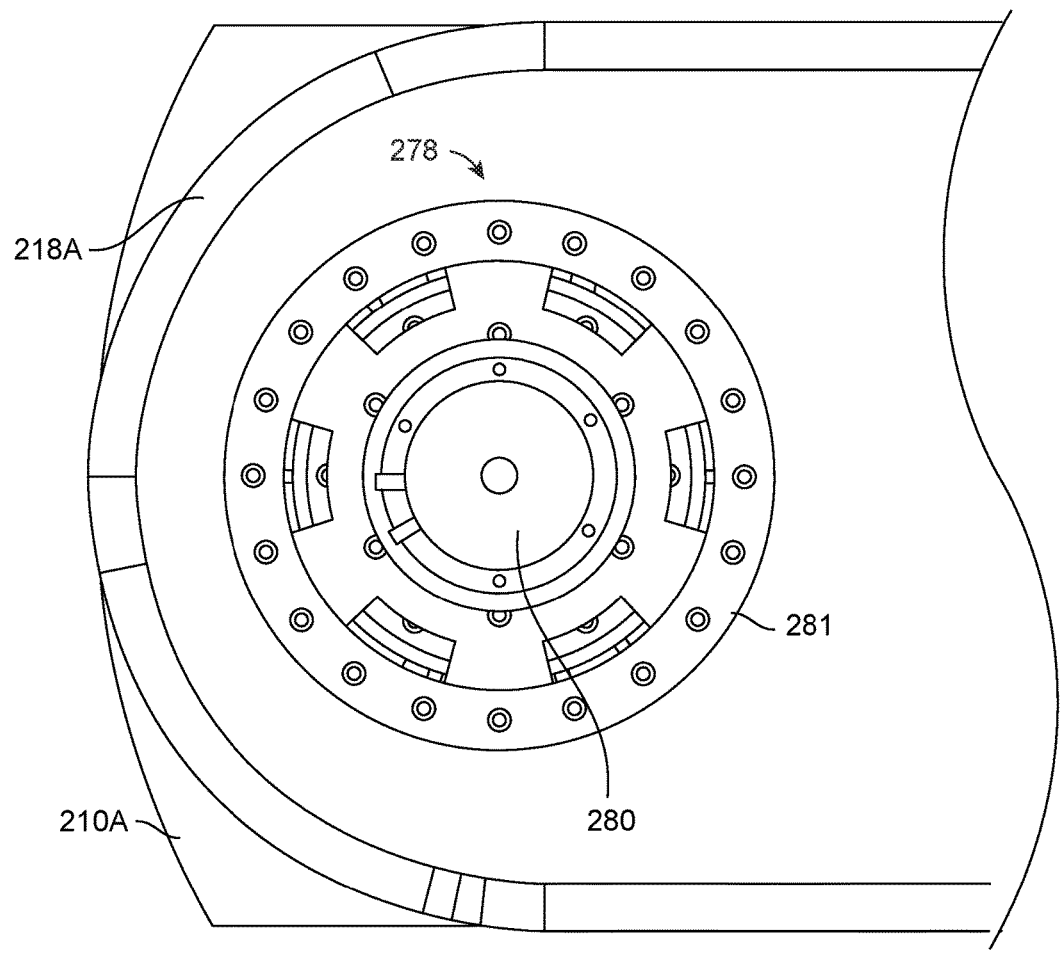
FIG. 2G is a bottom view of the swivel mechanism shown in FIG. 2E according to one embodiment.

FIG. 2G is a bottom view of the swivel mechanism shown in FIG. 2E according to one embodiment. The harmonic drive motor 280 is exposed such that electrical wires, e.g., from a column of the surgical robotics system, may be coupled to the harmonic drive motor 280 to provide control signals to the harmonic drive motor 280.

Figure 2H:
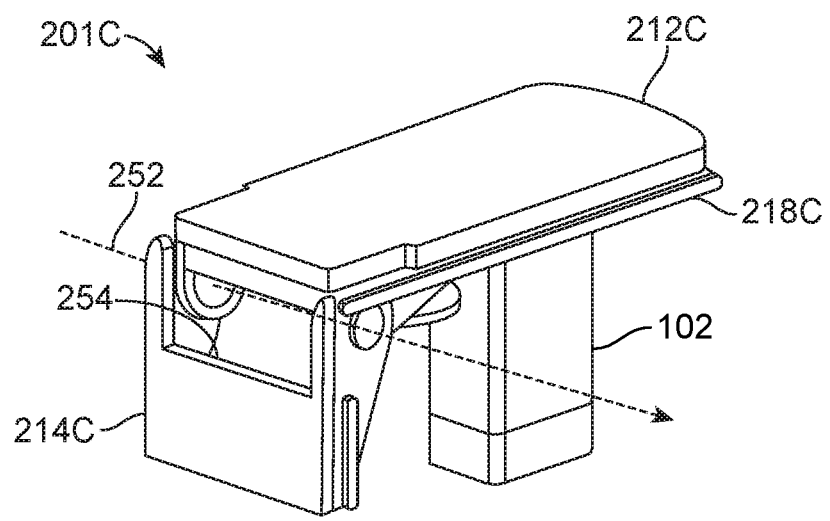
FIG. 2H is an isometric view of a folding segment of the table according to one embodiment.

FIG. 2H is an isometric view of a foldable segment 214C of a table 201C according to one embodiment. The table 201C is an embodiment of table 201A in FIG. 2A. The table 201C also includes a center segment 212C coupled to a table base 218C. The foldable segment 214C rotates using bearings about an axis 252 parallel to the table base 218C. The foldable segment 214C is rotated such that the foldable segment 214C is orthogonal to the table base 218C and the center segment 212C. In other embodiments, the foldable segment 214C may be rotated to other angles relative to the table base 218C and the center segment 212C. The foldable segment 214C includes a cutout section 254, for example, to provide greater access to a patient lying on the table 201C. In other embodiments, the foldable segment 214C does not include a cutout section.

Figure 2I:
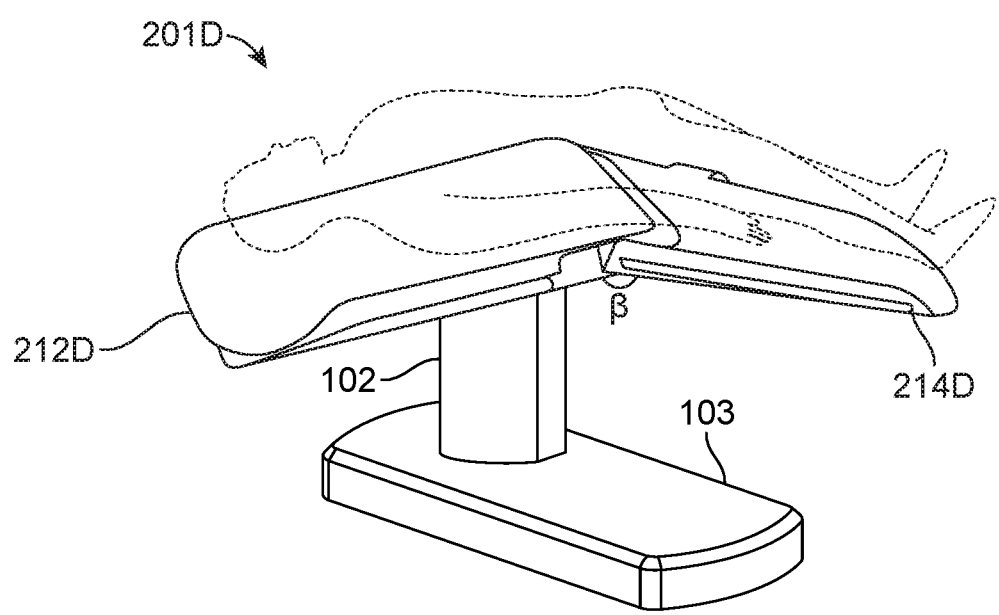
FIG. 2I is another isometric view of a folding segment of the table according to one embodiment.

FIG. 2I is another isometric view of a foldable segment 214D of a table 201D according to one embodiment. The table 201D is an embodiment of table 201A in FIG. 2A. The foldable segment 214D is rotated such that the foldable segment 214D and the table base 218D is positioned at an angle β relative to each other. The table 201D includes a mechanism for the foldable segment 214D and the center segment 212D to maintain the rotated position while supporting the weight of a patient on the table 201D. For example, the mechanism is a friction brake at the joint of the foldable segment 214D and the center segment 212D that holds the two segments at the angle β. Alternatively, the foldable segment 214D rotates about the center segment 212D using a shaft and the mechanism is a clutch that locks the shaft, and thus keeps the two segments at a fixed position. Though not shown in FIG. 2I, the table 201D may include motors or other actuators to automatically rotate and lock the foldable segment 214D to a certain angle relative to the center segment 212D. Rotating the foldable segment 214D is advantageous, for example, because the corresponding configuration of the table 201D provides greater access to the area around the abdomen of a patient lying on the table 201D.

Figure 2J:
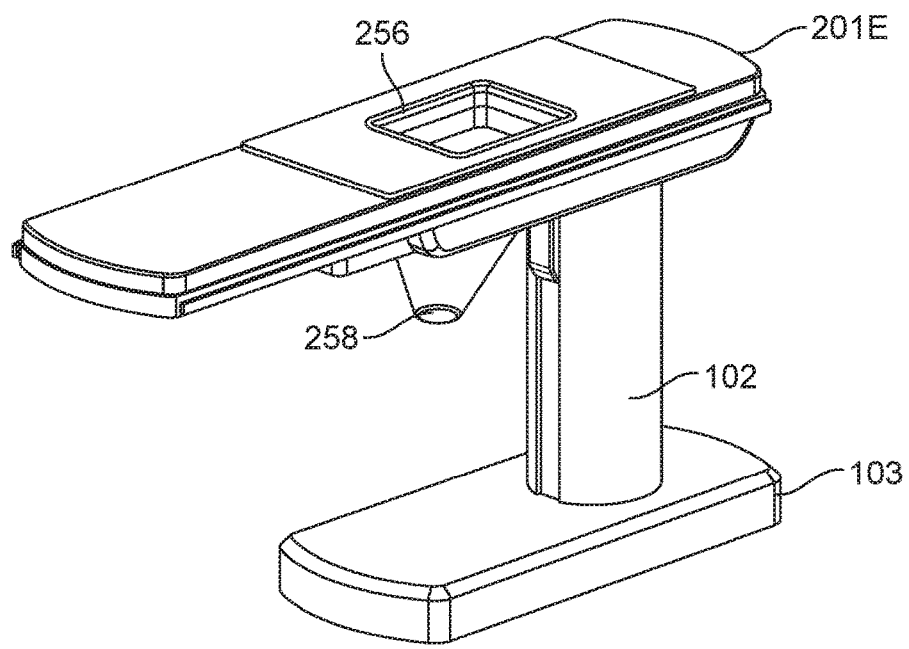
FIG. 2J is an isometric view of a trapdoor of the table according to one embodiment.

FIG. 2J is an isometric view of a trapdoor 256 of a table 201E according to one embodiment. The table 201E is an embodiment of table 201A in FIG. 2A. Specifically, the table 201E includes the trapdoor 256 and a drainage component 258 positioned below the trapdoor 256. The trapdoor 256 and drainage component 258 collect waste materials such as fluid (e.g., urine), debris (e.g., feces) that are secreted or released by a patient lying on the table during a surgical procedure. A container (not shown) may be positioned below the drainage component 258 to collect and store the waste materials. The trapdoor 256 and drainage component 258 are advantageous because they prevent waste materials from soiling or de-sterilizing equipment such as other components of the surgical robotic system 100 or other surgical tools in an operating room with the surgical robotic system 100.

Figure 2K:
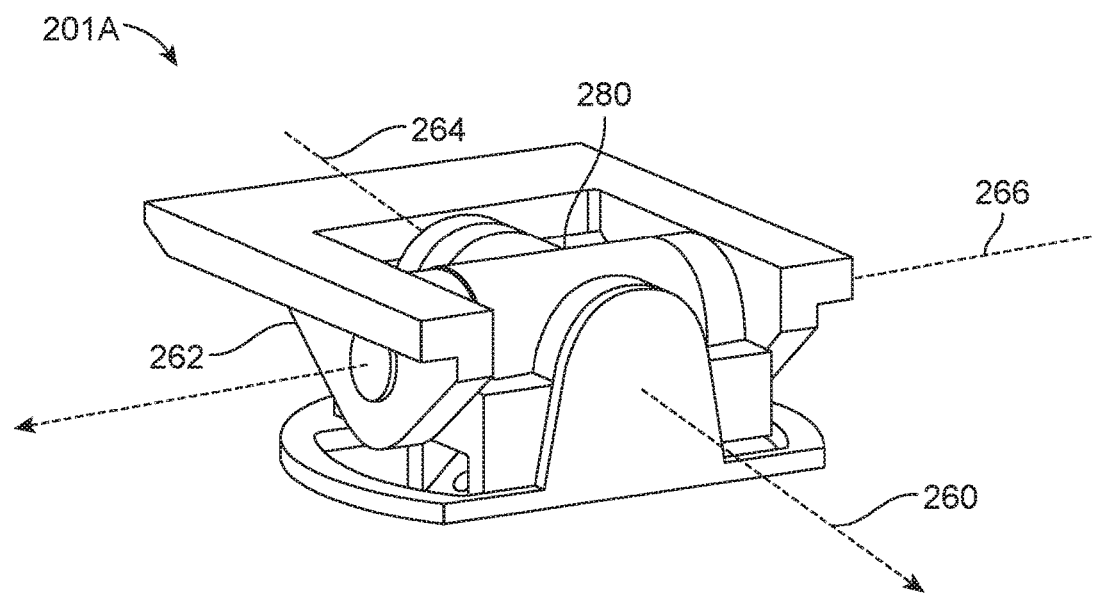
FIG. 2K is an isometric view of pivots of the table according to one embodiment.

FIG. 2K is an isometric view of pivots of the table 201A according to one embodiment. Specifically, the table 201A includes a first pivot 260 and a second pivot 262. The table 201A rotates about a first axis 264. A user, e.g., a physician, may rotate the table 201A about the first axis 264 or the second axis 266 manually or assisted by the surgical robotics system 100. The surgical robotics system 100 may also rotate the table 201A automatically, for example, by using control signals to operate a motor coupled to the first pivot 260 or the second pivot 262. The motor 280 is coupled to the first pivot 260. Rotation of the table 201A may provide greater access to certain areas of a patient lying on the table 201A during a surgical procedure. Specifically, the table 201A is configured to orient a patient lying on the table 201A in a Trendelenburg position by rotating about the first axis 264. Rotation of the table 201A is further described in FIGS. 2L-M.

Figure 2L:
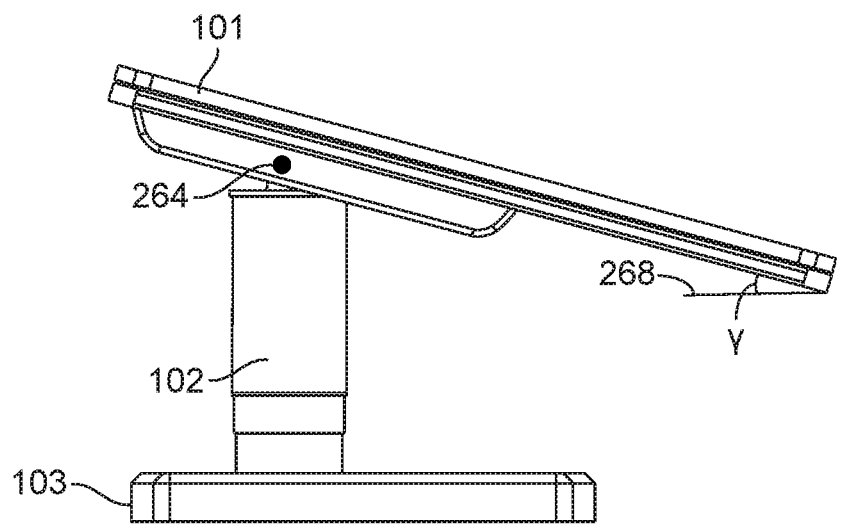
FIG. 2L is a side view of the table rotated about an axis of pitch according to one embodiment.

FIG. 2L is a side view of the table 201A rotated about the axis of pitch 264 according to one embodiment. Specifically, the table 201A is rotated to an angle γ relative to a plane 268 parallel to the ground.

Figure 2M:
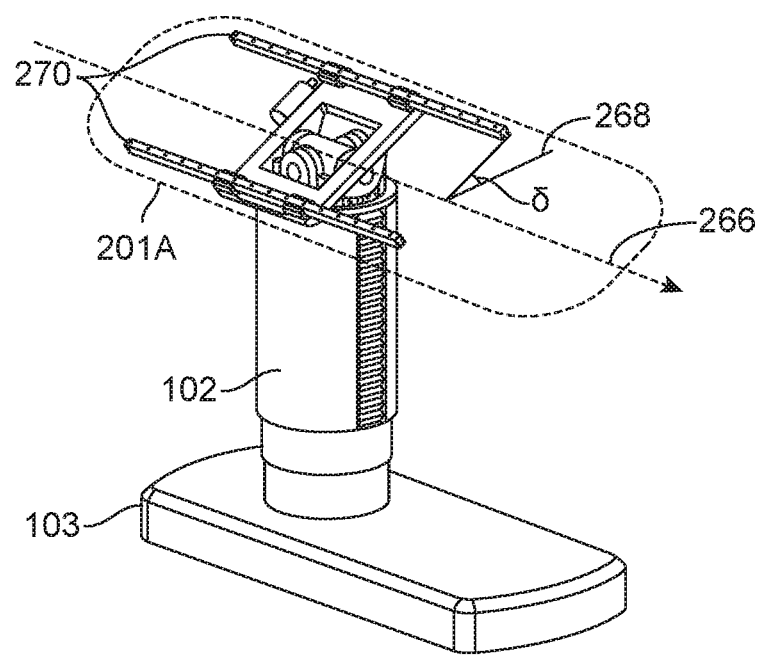
FIG. 2M is an isometric view of the table rotated about an axis of row according to one embodiment.

FIG. 2M is an isometric view of the table 201A rotated about the axis of row 266 according to one embodiment. Specifically, the table 201A is rotated to an angle δ relative to the plane 268 parallel to the ground. The table 201A is illustrated as transparent to expose components underneath the table 201A. The table includes a set of rails 270. The table 201A may translate laterally along an axis 266 parallel to the set of rails 270. The surgical robotics system 100 translates the table 201A laterally using, for example, a motor or other means of actuation (not shown). A user of the surgical robotics system 100 may also manually translate the table 201A, or with assistance from the surgical robotics system 100.

Alternative views and embodiments of the table 201A including the above mentioned components are further illustrated and described at least in U.S. Provisional Application No. 62/235,394 filed Sep. 30, 2015.

III. Column

Figure 3A:
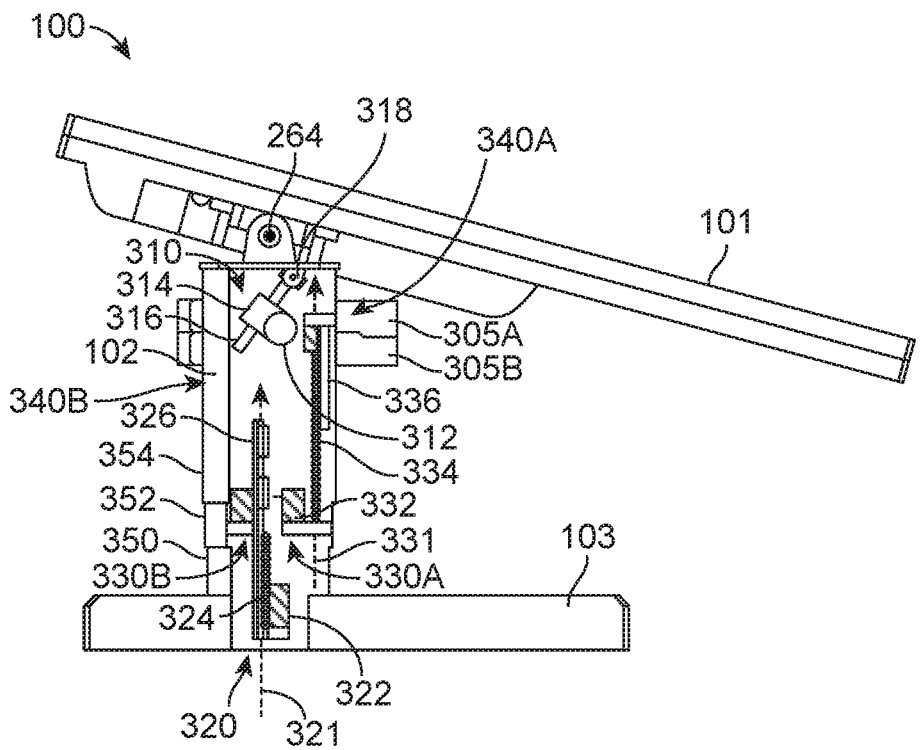
FIG. 3A is a side cutaway view of a column of the surgical robotics system according to one embodiment.

FIG. 3A is a side cutaway view of the column 102 of the surgical robotics system 100 according to one embodiment. The column 102 includes electrical and mechanical and other types of components to perform functions of the surgical robotics system 100. The column 102 includes a pitch rotation mechanism 310, column telescoping mechanism 320, ring telescoping mechanisms 330A and 330B, and ring rotation mechanisms 340A and 340B. The ring rotation mechanisms 340A and 340B are further described in FIG. 3B.

The surgical robotics system 100 rotates the table 101 about the axis of pitch 264 (also illustrated previously in FIGS. 2K-L) using the pitch rotation mechanism 310. The pitch rotation mechanism 310 includes a pitch rotation motor 312, right angle gearbox 314, pitch rotation lead screw 316, and pitch rotation bracket 318. The pitch rotation motor 312 is coupled to the right angle gearbox 314. The pitch rotation motor 312 is orthogonal to the pitch rotation lead screw 316. The pitch rotation lead screw 316 is movably coupled to the pitch rotation bracket 318. The right angle gearbox 314 is coupled to the pitch rotation lead screw 316. Output rotation of the pitch rotation motor 312 causes translational motion of the pitch rotation lead screw along an axis 311. Accordingly, translational motion of the pitch rotation lead screw 318 causes the table 101 to rotate about the axis of pitch 264.

The surgical robotics system 100 translates the table vertically using the column telescoping mechanism 320. The column telescoping mechanism 320 includes a column telescoping motor 322, column telescoping lead screw 324, and column telescoping rail 326. The column telescoping motor 322 is coupled to the column telescoping lead screw 324. The column telescoping motor 322 and the column telescoping lead screw 324 are stationary relative to the base 103. The column telescoping lead screw 324 is engaged with the column telescoping rail 326. Output rotation of the column telescoping motor 322 causes the column telescoping rail 326 to translate along a vertical axis 321 along the column telescoping lead screw 324. As the column telescoping rail 326 translates in the positive direction along the vertical axis 321, the height of the column 102 and the table 101 increases.

The column 102 also includes a lower column segment 350, middle column segment 352, and upper column segment 354. The lower column segment 350 is coupled to the base 103 and stationary relative to the base 103. The middle column segment 352 is movably coupled to the lower column segment 350. The upper column segment 354 is movably coupled to the middle column segment 352. In other embodiments, a column 102 may include additional or fewer column segments.

The upper column segment 354 and/or the middle column segment 352 also translate along the vertical axis 321 to extend the height of the column 102. Similarly, as the column telescoping rail 326 translates in the negative direction along the vertical axis 321, the height of the column 102 and the table 101 decreases. Further, the upper column segment 354 and/or the middle column segment 352 also translate along the vertical axis 321, collapsing over the lower column segment 350. A table 101 with adjustable height is advantageous because the table 101 facilitates a variety of surgical procedures. Specifically, one surgical procedure requires a patient lying on the table 101 to be positioned at a height lower than the height of a patient lying on the table 101 for a different surgical procedure. In some embodiments, the column telescoping mechanism 320 uses other means of actuation such as hydraulics or pneumatics instead of—or in addition to—motors.

The surgical robotics system 100 translates column rings 305A and 305B vertically using the ring telescoping mechanisms 330A and 330B. The ring telescoping mechanism 330A includes a ring telescoping motor 332, ring telescoping lead screw 334, and ring telescoping rail 336. Column rings are further described with reference to FIGS. 5A-E in Section V. Column Ring. Column rings 305A and 305B are movably coupled to the column 102 and translate along a vertical axis 331. Generally, a column 102 includes a ring telescoping mechanism for each column ring of the column 102. Specifically, the column 102 includes ring telescoping mechanism 330A and second ring telescoping mechanism 330B. The ring telescoping motor 332 is coupled to the ring telescoping lead screw 334. The ring telescoping motor 332 and the ring telescoping lead screw 334 are stationary relative to the base 103. The ring telescoping lead screw 334 is engaged with the ring telescoping rail 336. The ring telescoping rail 336 is coupled to the column ring 305A. Output rotation of the ring telescoping motor 332 causes the ring telescoping rail 336 to translate along the vertical axis 331 and along the ring telescoping lead screw 334. As the ring telescoping rail 336 translates in the positive direction or negative direction along the vertical axis 331, the height of a corresponding column ring increases or decreases, respectively.

Figure 3B:
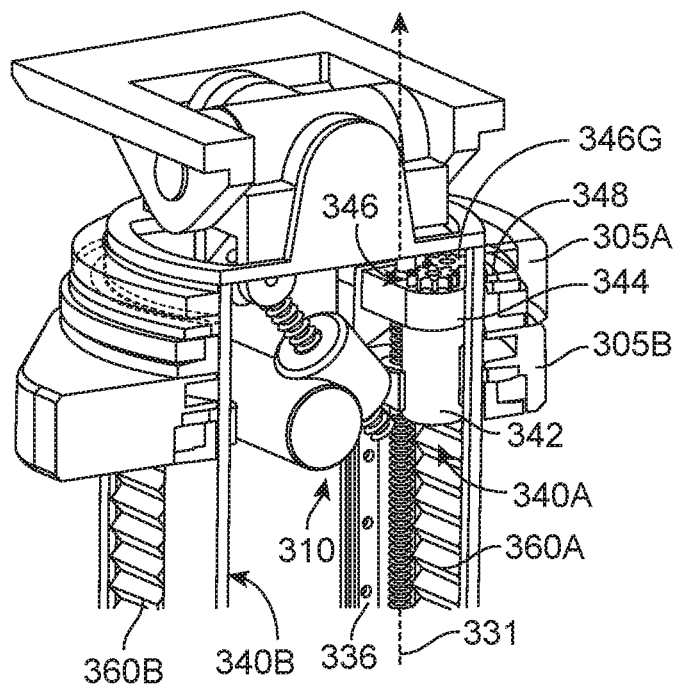
FIG. 3B is an isometric cutaway view of the column according to one embodiment.

FIG. 3B is an isometric cutaway view of the column 102 according to one embodiment. The column 102 includes a first accordion panel 360A and a second accordion panel 360B. The accordion panels 360A and 360B extend or fold as the surgical robotics system 100 translates column rings 305A and 305B in the positive direction or negative direction along the vertical axis 331, respectively. The accordion panels 360A and 360B are advantageous because they protect electrical and mechanical and other types of components inside the column 102 (e.g., the pitch rotation mechanism 310, column telescoping mechanism 320, ring telescoping mechanisms 330A and 330B, and ring rotation mechanisms 340A and 340B) from becoming soiled or de-sterilized by fluid waste and other hazards. FIG. 3B shows an isometric view of the ring rotation mechanism 340A, while the ring rotation mechanism 340B is obscured by the column 102.

The surgical robotics system 100 rotates column rings 305A and 305B using the ring rotation mechanisms 340A and 340B, respectively. The ring telescoping rail 336 is coupled to the ring rotation motor 342 by a ring rotation bracket 344. The ring rotation motor 342 is coupled to a set of gears 346. The set of gears 346 includes a driving gear 346G. The driving gear 346G is engaged with a column ring rail 348 of the column ring 305A. Output rotation of the ring rotation motor 342 causes the set of gears 346 and the driving gear 346G to rotate. Accordingly, the rotation of the driving gear 346G causes the column ring 305A to rotate about a vertical axis 341 concentric to the column 102. The column 102 includes another ring rotation mechanism 340B corresponding to the column ring 305B. Generally, both ring rotation mechanisms 340A and 340B and column rings 305A and 305B will be substantially the same, however in other implementations they may be constructed using different mechanisms.

Figure 3C:
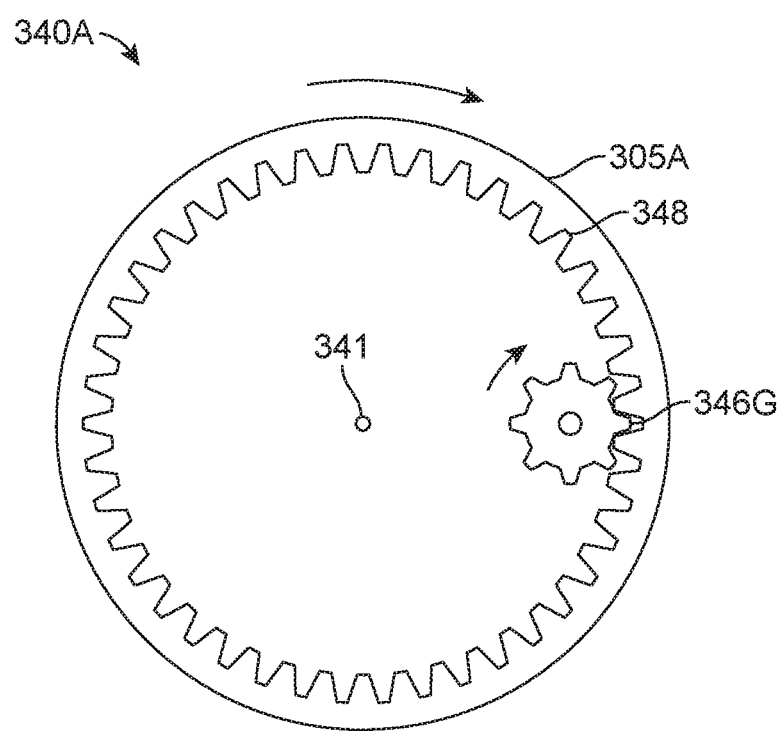
FIG. 3C is a top view of the column according to one embodiment.

FIG. 3C is a top view of the ring rotation mechanism 340A according to one embodiment. For purposes of clarity, FIG. 3C only shows the driving gear 346G, the column ring 305A, and the column ring rail 348 of the ring rotation mechanism 340A. In an example use case, the surgical robotics system 100 rotates the driving gear 346G clockwise to rotate the column ring rail 348—and thus, the column ring 305A—clockwise about the vertical axis 341.

Alternative views and embodiments of the column 103 including the above mentioned components are further illustrated and described at least in U.S. Provisional Application No. 62/162,486 filed May 15, 2015 and U.S. Provisional Application No. 62/162,467 filed May 15, 2015.

IV. Column-Mounted Robotic Arms

Figure 4A:
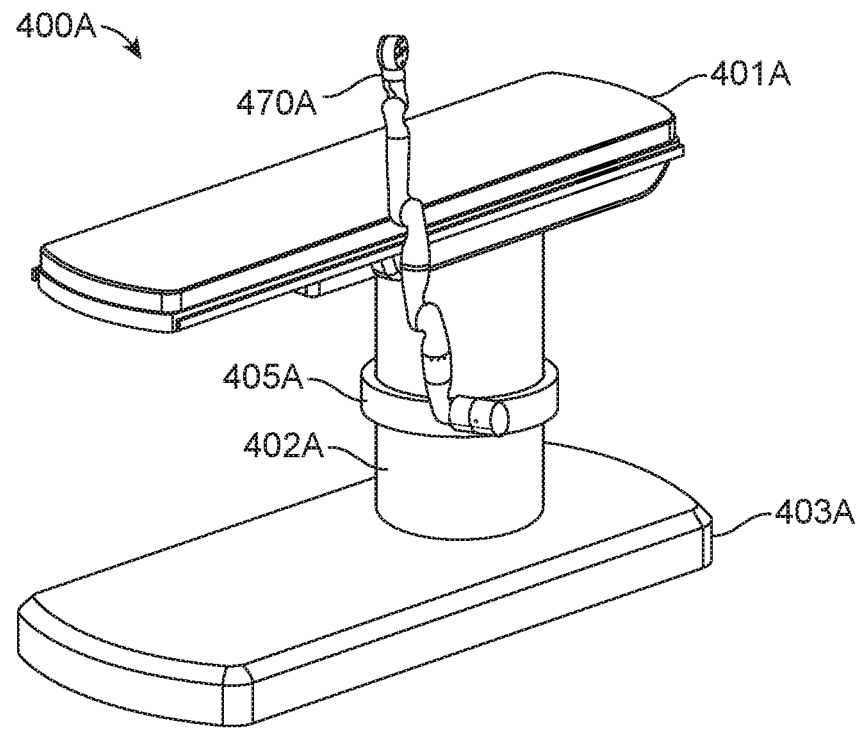
FIG. 4A is an isometric view of a surgical robotics system with a column-mounted robotic arm according to one embodiment.

FIG. 4A is an isometric view of a surgical robotics system 400A with a column-mounted robotic arm 470A according to one embodiment. The surgical robotics system 400A includes a set of robotic arms, a set of column rings, table 401A, column 402A, and base 403A. The surgical robotics system 400A is an embodiment of the surgical robotics system 100 shown in FIG. 1. Generally, the set of robotics arms includes one or more robotic arms, such as robotic arm 470A, where the robotic arms are coupled to one or more column rings, such as column ring 405A. Column rings are described in more detail with respect to FIGS. 5A-E in Section V. Column Ring below. Robotic arms are described in more detail with respect to FIGS. 6A-C in Section VI. Robotic Arm below. Column rings 405A are movably coupled to the column 402A. Thus, a robotic arm 470A attached to a column 405A may be referred to as a column-mounted robotic arm 470A. As introduced above, the surgical robotics system 400A uses robotic arms 470A to perform surgical procedures on a patient lying on the table 401A.

Figure 4B:
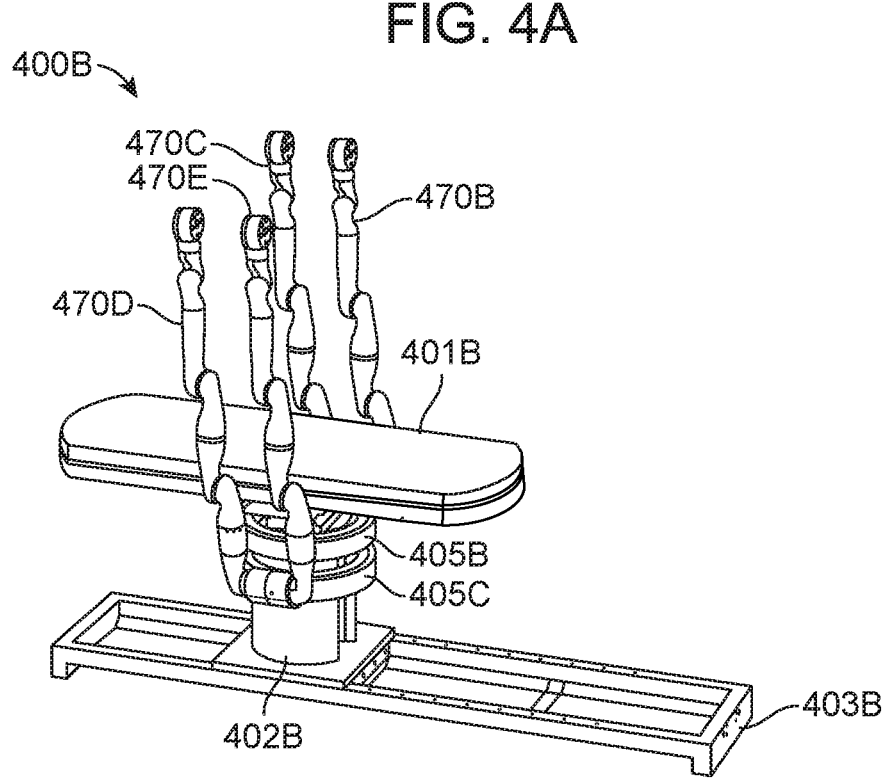
FIG. 4B is an isometric view of a surgical robotics system with column-mounted robotic arms according to one embodiment.

FIG. 4B is an isometric view of a surgical robotics system 400B with column-mounted robotic arms according to one embodiment. The surgical robotics system 400B is an embodiment of the surgical robotics system 400A shown in FIG. 4A. The surgical robotics system 400B includes multiple robotic arms, i.e., a first robotic arm 470B, second robotic arm 470C, third robotic arm 470D, and fourth robotic arm 470E, as well as multiple column rings, i.e., a first column ring 405B and second column ring 405C. In other embodiments, the surgical robotics system 400B may include additional or fewer robotic arms and/or column rings. Further, the robotic arms may be coupled to column rings in various configurations. For example, three robotic arms may be coupled to a column ring. Additionally, the surgical robotics system 400B may include three column rings each coupled to two robotic arms.

Alternative views and embodiments of the surgical robotics system 400B including the above mentioned components with column-mounted robotic arms are further illustrated and described at least in U.S. Provisional Application No. 62/162,486 filed May 15, 2015 and U.S. Provisional Application No. 62/162,467 filed May 15, 2015.

V. Column Ring

Figure 5A:
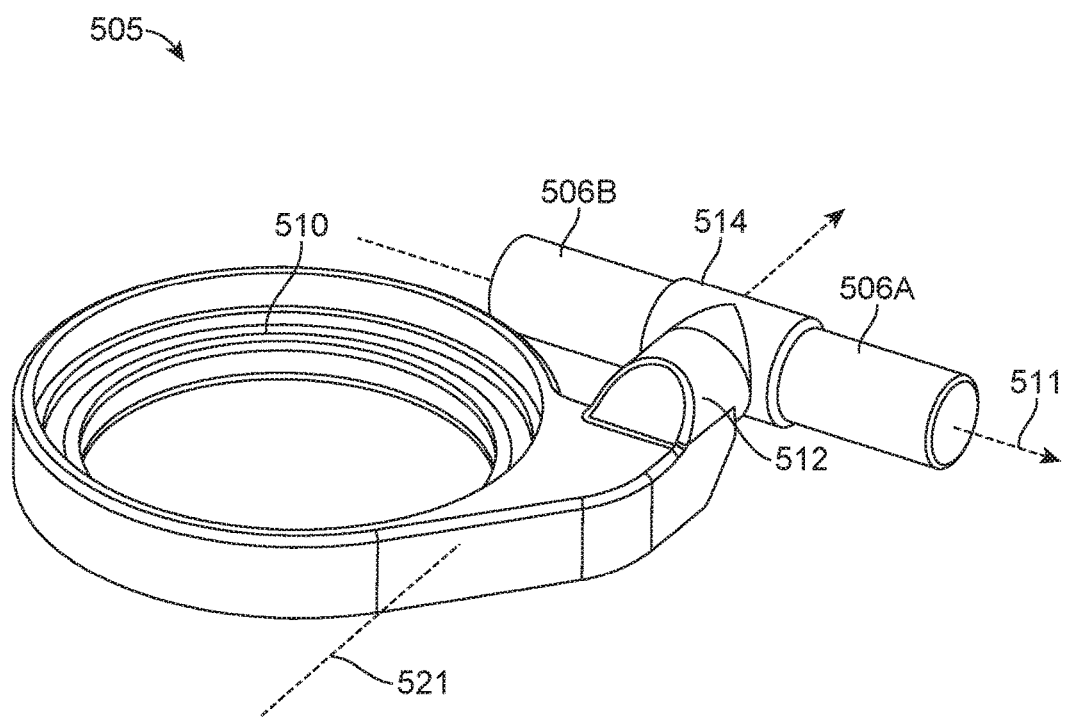
FIG. 5A is an isometric view of a column ring of the surgical robotics system according to one embodiment.

FIG. 5A is an isometric view of a column ring 505 of a surgical robotics system—for example, surgical robotics system 100, 400A, or 400B—according to one embodiment.

The column ring 505 includes a column ring rail 510, arm mount pivot 512, arm mount base 514, and a set of arm mounts. The set of arm mounts includes one or more arm mounts. Specifically, the set of arm mounts in FIG. 5A includes a first arm mount 506A and a second arm mount 506B. Generally, each arm mount of the set of arm mounts and the arm mount base 514 are cylindrically shaped.

The first arm mount 506A and the second arm mount 506B are movably coupled the arm mount base 514. The first arm mount 506A and the second arm 506B mount may rotate—together or independently—about the axis 511 concentric to the arm mount base 514. For example, the surgical robotics system 400B rotates the first arm mount 506A and the second arm mount 506B using a motor or other means of actuation (not shown) inside the arm mount base 514 or arm mounts. In some embodiments, the first arm mount 506A and the second arm mount 506B rotate at predetermined increments, e.g., increments of 15 degrees.

The arm mount base 514 is coupled to the arm mount pivot 512. The arm mount pivot 512 uses a motor or other means of actuation (not shown) inside the arm mount pivot 512 to rotate the arm mount base 514 about the axis 521 orthogonal to the axis 511. The arm mount pivot 512 is coupled to, and stationary relative to, the column ring rail 510. Rotating the arm mount base 514 is advantageous because robotic arms (and arm mounts) coupled to the arm mount base 514 may be reoriented in response to rotation of the table 401B. Accordingly, robotic arms coupled to the arm mounts of the arm mount base 514 have greater access to a patient lying on the table 401B.

Figure 5B:
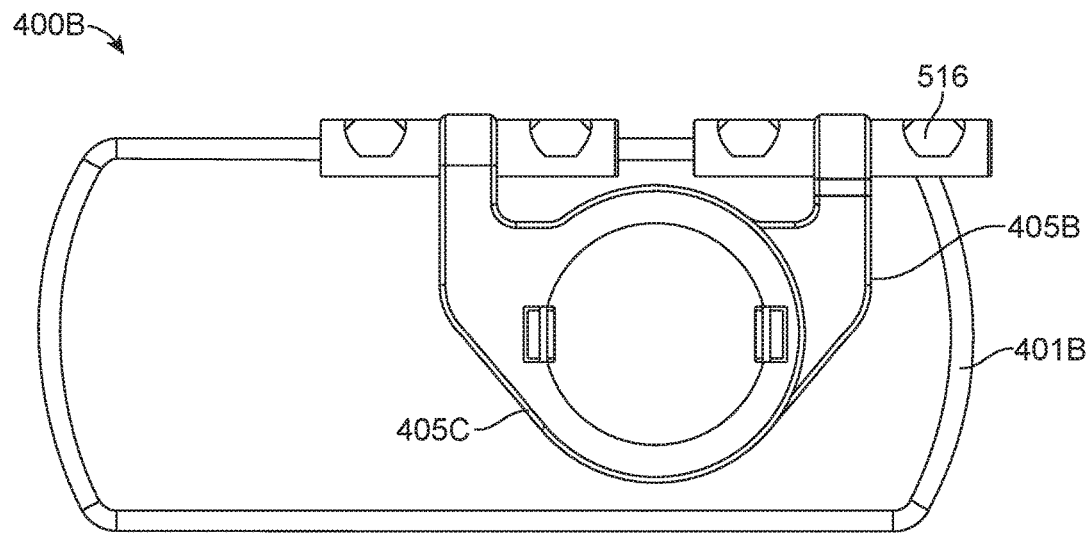
FIG. 5B is a bottom view of a set of column rings underneath a table according to one embodiment.

FIG. 5B is a bottom view of the set of column rings underneath the table 401B of FIG. 4B according to one embodiment. The set of column rings includes the first column ring 405B and the second column ring 405C. Note that FIG. 5B shows the first column ring 405B and the second column ring 405C aligned such that the arm mounts are on the same side of the table 401B, while FIG. 4B shows the first column ring 405B and the second column ring 405C positioned such that the arm mounts are on opposite sides of the table 401B. The surgical robotics system 400B may rotate the column rings 405B and 405C to position the arm mounts in other configurations. For example, two arm mounts are positioned on one side of the table 401B and two arm mounts are positioned on an opposite side of the table 401B. By rotating column rings independently from each other around the column, the surgical robotics system 400B may configure the arm mounts—and thus, robotic arms mounted to the arm mounts—in a greater number of possible positions. Due to this configurability, the surgical robotics system 400B accommodates a variety of surgical procedures because the robotic arms can access any area (e.g., upper body, core body, or lower body) of the body of a patient lying on the table 401B. In some embodiments, each arm mount of the column rings include a notch 516 which facilitates the attachment of a robotic arm to the arm mount.

Figure 5C:
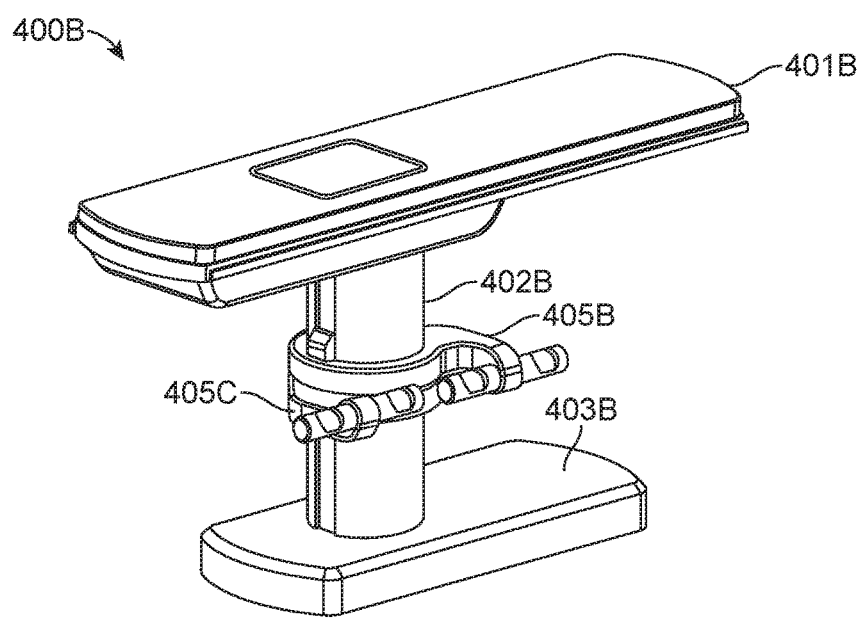
FIG. 5C is an isometric view of the set of column rings mounted to a column according to one embodiment.

FIG. 5C is an isometric view of the set of column rings mounted to the column 402B of FIG. 4B according to one embodiment. Similarly to FIG. 5B, FIG. 5C shows all the arm mounts aligned on the same side of the surgical robotics system 400B.

Figure 5D:
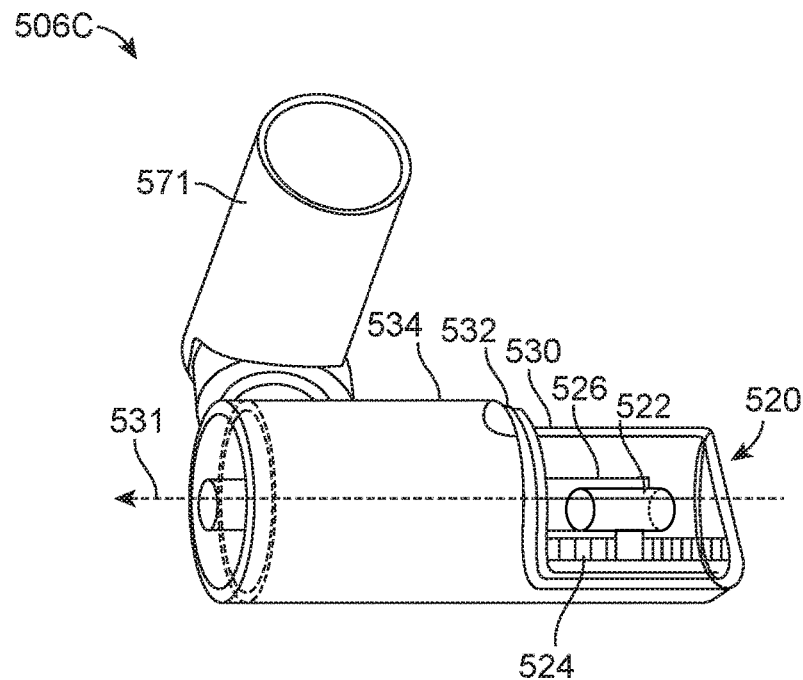
FIG. 5D is an isometric cutaway view of an arm mount of a column ring according to one embodiment.

FIG. 5D is an isometric cutaway view of an arm mount 506C of a column ring according to one embodiment. The arm mount 506C includes an arm mount telescoping mechanism 520 and a set of arm mount segments. The arm mount telescoping mechanism 520 includes an arm mount telescoping motor 522, arm mount telescoping lead screw 524, and arm mount telescoping rail 526. Generally, the set of arm mount segments includes one or more arm mount segments. Specifically, the set of arm mount segments in FIG. 5D includes a lower arm mount segment 530, middle arm mount segment 532, and upper arm mount segment 534. A robotic arm segment 571 (e.g., of the robotic arm 470B in FIG. 4B) is coupled to the upper arm mount segment 534. The middle arm mount segment 532 and the upper arm mount segment 534 are movably coupled to the lower arm mount segment 530. The lower arm mount segment 530 is coupled to an arm mount base (e.g., arm mount base 514 in FIG. 5A).

The surgical robotics system 400B translates the arm mount 506C along an axis 531 using the arm mount telescoping mechanism 520. In FIG. 5D, the axis 531 is in a horizontal orientation, though it should be noted that, in other embodiments, the axis 531 is in a vertical or any other orientation. The arm mount telescoping motor 522 is coupled to the arm mount telescoping rail 526. The arm mount telescoping rail 526 is engaged with the arm mount telescoping lead screw 524. The arm mount telescoping lead screw 524 is stationary relative to the lower arm mount segment 530. Output rotation of the arm mount telescoping motor 522 causes the arm mount telescoping rail 526 to translate along the vertical axis 531. Translation of the arm mount 506C is advantageous because, if the arm mount 506C is extended, a robotic arm mounted to the arm mount 506C may have greater access to a patient lying on the table 401B during a surgical procedure.

Figure 5E:
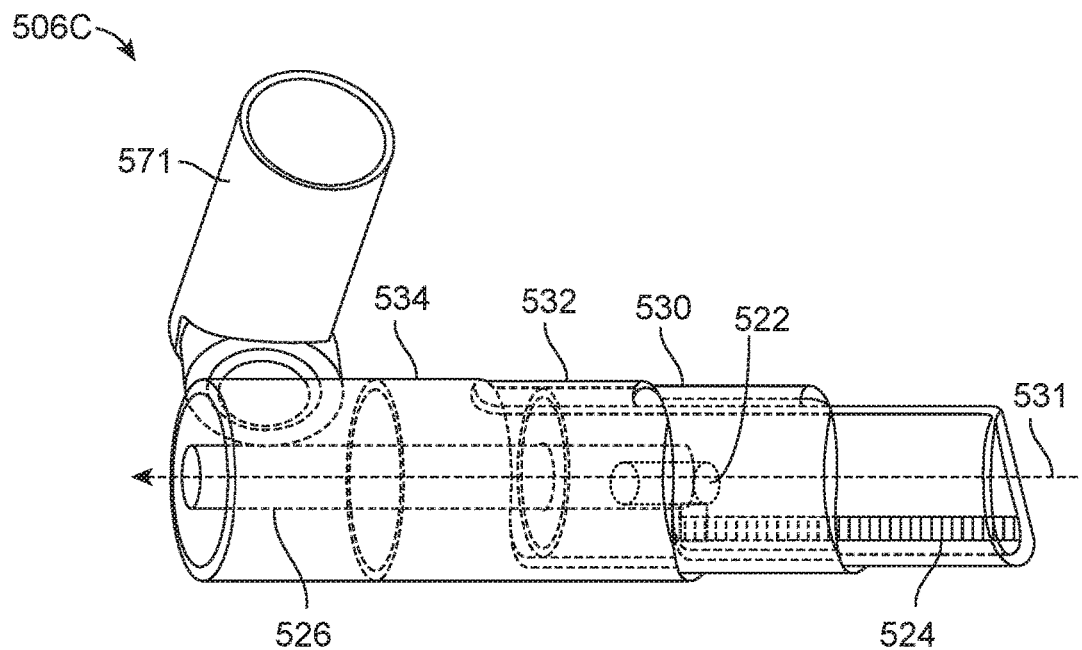
FIG. 5E is an isometric cutaway view of the arm mount in a telescoped configuration according to one embodiment.

FIG. 5E is an isometric cutaway view of the arm mount 506C in a telescoped configuration according to one embodiment. In the telescoped configuration, the upper arm mount segment 534 and the middle arm mount segment 532 extend in the positive axis 531 direction to facilitate extension of the arm mount 506C.

Alternative views and embodiments of the column ring 505 including the above mentioned components are further illustrated and described at least in U.S. Provisional Application No. 62/162,486 filed May 15, 2015 and U.S. Provisional Application No. 62/162,467 filed May 15, 2015.

VI. Robotic Arm

Figure 6A:
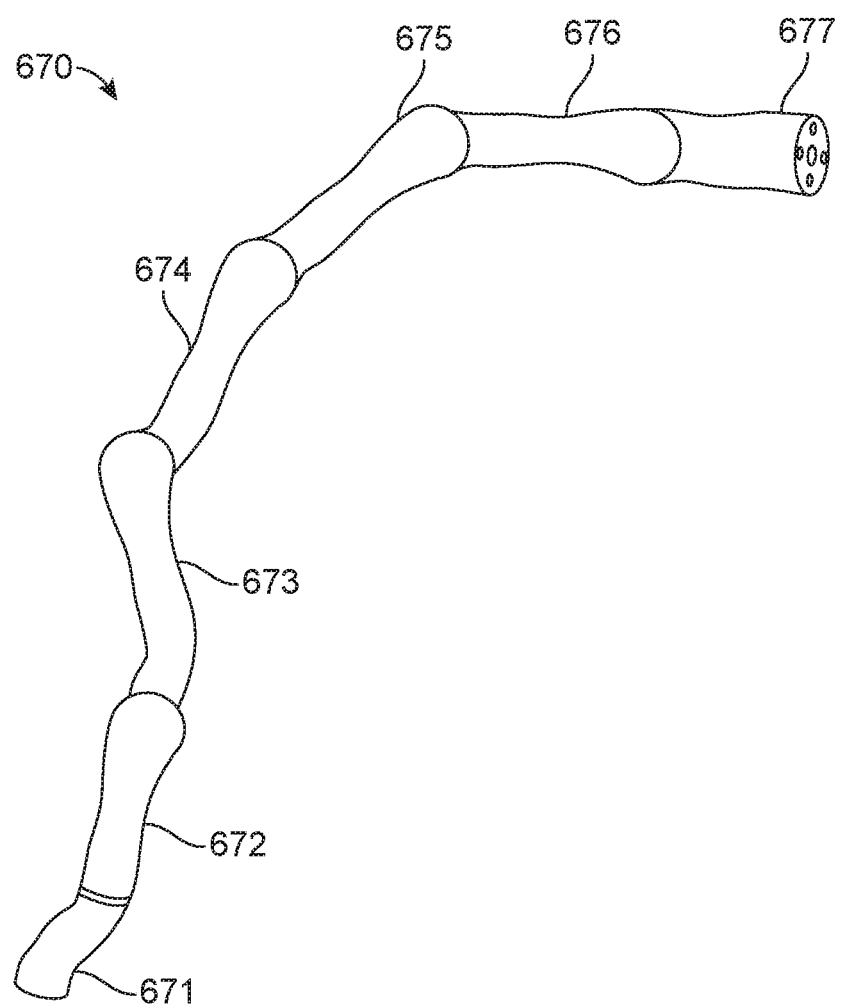
FIG. 6A is an isometric view of a robotic arm of the surgical robotics system according to one embodiment.

FIG. 6A is an isometric view of a robotic arm 670 of a surgical robotics system—for example, surgical robotics system 100, 400A, or 400B—according to one embodiment. Generally, the robotic arm 670 includes a set of robotic arm segments such as robotic arm segments 671, 672, 673, 674, 675, 676, and 677. Each arm segment is movably coupled to at least one other arm segment at an arm segment joint. In particular, the first arm segment 671 is movably coupled to the second arm segment 672, the second arm segment 672 is movably coupled to the third arm segment 673, and so forth. The first arm segment 671 is movably coupled to an arm mount (e.g., arm mount 506A in FIG. 5A). The seventh arm segment 677 (or the last arm segment of a set of arm segments including a number of arm segments different than seven), is coupled to a surgical instrument. The seventh arm segment 677 may also include mechanisms to hold a surgical instrument such as a clamp or robotic fingers. The robotic arm 670 uses electrical and mechanical components, such as motors, gears, and sensors, inside the robotic arm segments to rotate the arm segments at the arm segment joints.

The robotic arm 670 receives control signals from a robotic arm control system, for example, housed in the column 402B in FIG. 4B. In some embodiments, the robotic arm 670 receives control signals from a robotic arm control system located outside of the column 402B or separate from the surgical robotics system 400B. Generally, the robotic arm 670 may include sensors that provide sensor data to the robotic arm control system. Specifically, pressure sensors provide force feedback signals and encoders or potentiometers provide measurements of rotation of arm segments. The robotic arm control system uses the sensor data to generate the control signals provided to the robotic arm 670. Since each arm segment may rotate with respect to another adjacent segment, each arm segment provides an additional degree of freedom to the mechanical system of the robotic arm 670. By rotating the robotic arm segments, the surgical robotics system 400B positions a surgical instrument coupled to the robotic arm 670 such that the surgical instrument has access to a patient undergoing a surgical procedure. Configurations of robotic arms of the surgical robotics system 400B are further described with reference to FIGS. 7A-F in Section VII. System Orientations for Performing Surgical Procedures.

Figure 6B:
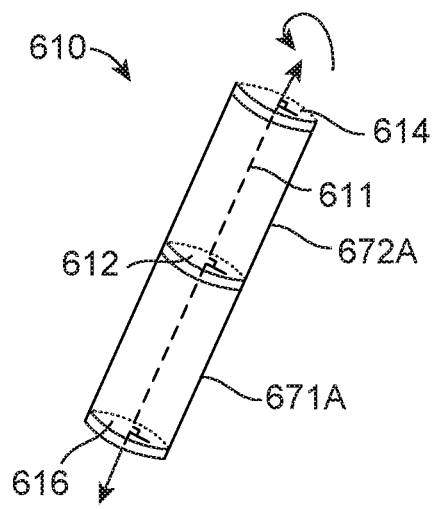
FIG. 6B is an isometric view of an arm segment joint of the robotic arm according to one embodiment.

FIG. 6B is an isometric view of an arm segment joint 610 of the robotic arm 670 according to one embodiment. The first arm segment 671A and the second arm segment 672A are embodiments of any of the arm segments in FIG. 6A. The arm segments 671A and 672A are cylindrically shaped and joined at the plane 612. The first arm segment 671A rotates relative to the second arm segment 672A about an axis 611 perpendicular to the plane 612. Further, the axis 611 is perpendicular to the plane 614 of the second arm segment 672A and perpendicular to the plane 616 of the first arm segment 671A. That is, the axis 611 is longitudinal relative to the arm segments 671A and 672A.

Figure 6C:
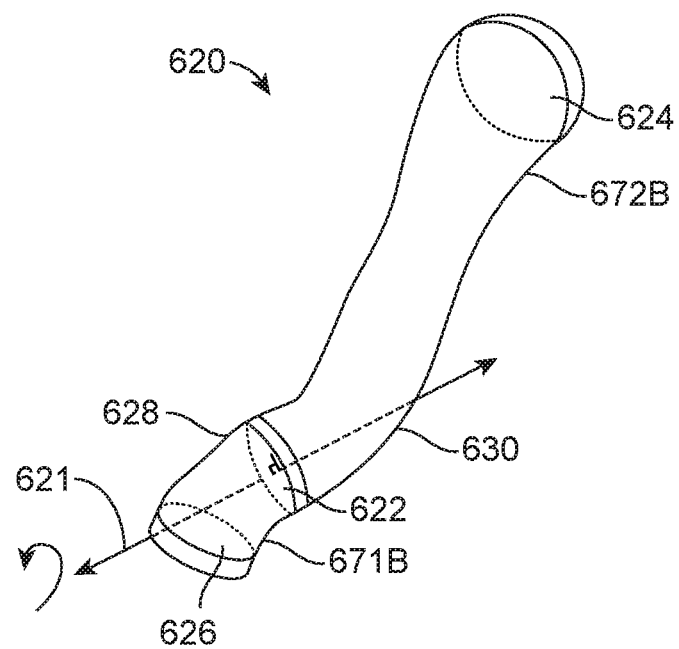
FIG. 6C is an isometric view of another arm segment joint of the robotic arm according to one embodiment.

FIG. 6C is an isometric view of another arm segment joint 620 of the robotic arm 670 according to one embodiment. The arm segments 671B and 672B are joined at the plane 622. Unlike the cylindrically shaped arm segments shown in FIG. 6B, the arm segments 671B and 672B each include a curved section 628 and 630, respectively. The first arm segment 671B rotates relative to the second arm segment 672B about an axis 621 perpendicular to the plane 622. The axis 621 is not perpendicular to the plane 624 of the arm segment 672B and not perpendicular to the plane 626 of the arm segment 671B. In some embodiments, the axis of rotation is perpendicular to a plane of one arm segment, but not perpendicular to a plane of the other arm segment of an arm segment joint.

Alternative views and embodiments of the robotic arm 670 including the above mentioned components are further illustrated and described at least in U.S. Provisional Application No. 62/162,486 filed May 15, 2015 and U.S. Provisional Application No. 62/162,467 filed May 15, 2015.

VII. System Orientations for Performing Surgical Procedures

The surgical robotics system 400B in FIG. 4B performs a variety of surgical procedures using column-mounted robotic arms of the set of robotic arms. The surgical robotics system 400B configures the column-mounted robotic arms to access portions of a patient lying on the table 401B before, during, and/or after a surgical procedure. The column-mounted robotic arms access portions near the groin of the patient for surgical procedures such as ureteroscopy, percutaneous nephrolithotomy (PCNL), colonoscopy, and fluoroscopy. The column-mounted robotic arms to access portions near the core (e.g., abdomen) area the patient for surgical procedures such as prostatectomy, colectomy, cholecystectomy, and inguinal hernia. The column-mounted robotic arms to access portions near the head of the patient for surgical procedures such as bronchoscopy, endoscopic retrograde cholangiopancreatography (ERCP).

The surgical robotics system 400B automatically reconfigures the column-mounted robotic arms, column rings, column, and table to perform different surgical procedures. The features of each subsystem and component of the surgical robotics system 400B enable the same set of robotics arms to access a large working volume, and multiple working volumes (based on the configuration), to perform a variety of surgical procedures on the patient. In particular, as mentioned above, the robotic arms may be configured in a first configuration to access the patients' groin area, in a second configuration to access the patients' abdomen area, and in a third configuration to access the patients' head area, in addition to other possible configurations. The degrees of freedom provided by the arm segments of the robotic arms, column rings, column, and table contribute to the wide range of configurations. The surgical robotics system 400B includes a computer system that stores computer program instructions, for example within a non-transitory computer-readable storage medium such as a persistent magnetic storage drive, solid state drive, etc. When executed by a processor of the computer system, the instructions cause the components of the surgical robotics system 400B to automatically reconfigure without the need for intervention, or with minimal intervention, from a user, e.g., a physician. For example, based on the instructions, the computer system sends an electronic control signal to motors of the robotics arms. In response to receiving the control signal, the motors rotate arm segments of the robotics arms into a certain position. The physician or another user may design a configuration of the surgical robotics system by creating the instructions and providing the instructions to the computer system. For example, the instructions are uploaded to a database of the computer system. The automatic configurability of the surgical robotics system 400B is an advantage because the automatic configurability saves resources. Specifically, the surgical robotics system 400B reduces the amount of time taken by users to setup the surgical robotics system 400B for a surgical procedure. Further, by using the surgical robotics system 400B for a variety of surgical procedures, users reduce the amount of surgical equipment that they need to purchase, maintain, store, and learn to operate.

Alternative views and embodiments of use cases of the surgical robotics system 400B with column-mounted robotic arms including the above mentioned components are further illustrated and described at least in U.S. Provisional Application No. 62/162,486 filed May 15, 2015 and U.S. Provisional Application No. 62/162,467 filed May 15, 2015.

VII. A. Lower Body Surgery

Figure 7A:
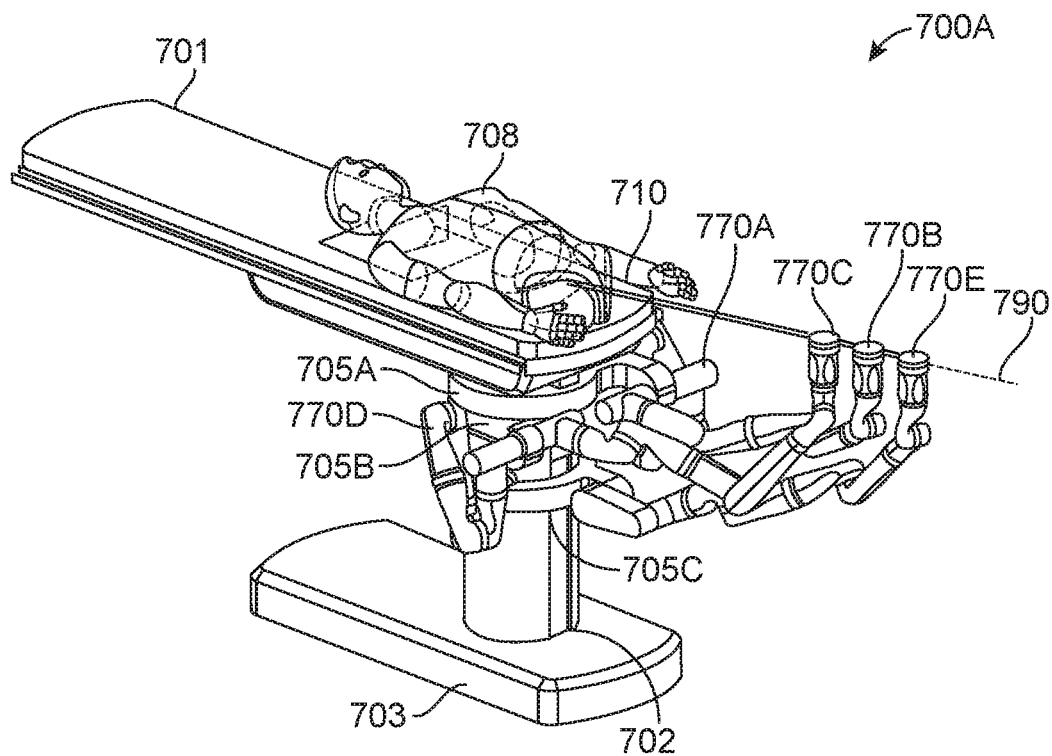
FIG. 7A is an isometric view of a surgical robotics system with column-mounted arms configured to access the lower body area of a patient according to one embodiment.

FIG. 7A is an isometric view of a surgical robotics system 700A with column-mounted arms configured to access the lower body area of a patient 708 according to one embodiment. The surgical robotics system 700A is an embodiment of—though includes more components than—the surgical robotics system 400B in FIG. 4B. Specifically, the surgical robotics system 700A includes a set of robotic arms (including five robotic arms in total) and a set of three column rings. A first robotic arm 770A and a second robotic arm 770B are coupled to a first column ring 705A. A third robotic arm 770C and a fourth robotic arm 770D are coupled to a second column ring 705B. A fifth robotic arm 770E is coupled to a third column ring 705C. FIG. 7A shows a wireframe of the patient 708 lying on the table 701 undergoing a surgical procedure, e.g., ureteroscopy, requiring access to the lower body area of the patient 708. Legs of the patient 708 are not shown as to not obscure portions of the surgical robotics system 700A.

The surgical robotics system 700A configures the set of robotic arms to perform a surgical procedure on the lower body area of the patient 708. Specifically, the surgical robotics system 700A configures the set of robotic arms to manipulate a surgical instrument 710. FIG. 7A shows the set of robotic arms inserting the surgical instrument 710 along a virtual rail 790 into the groin area of the patient 708. Generally, a virtual rail 790 is a co-axial trajectory along which the set of robotic arms translates a surgical instrument (typically a telescoping instrument). The second robotic arm 770B, the third robotic arm 770C, and the fifth robotic arm 770E are coupled, e.g., holding, the surgical instrument 710. The first robotic arm 770A and the fourth robotic arm 770D are stowed to the sides of the surgical robotics system because they are not necessarily required to for the surgical procedure—or at least part of the surgical procedure—shown in FIG. 7A. The robotic arms are configured such that they manipulate the surgical instrument 710 from a distance away from the patient 708. This is advantageous, for example, because there is often limited space available closer toward the patient's body or there is a sterile boundary around the patient 708. Further, there may also be a sterile drape around surgical equipment. During a surgical procedure, only sterile objects are allowed pass the sterile boundary. Thus, the surgical robotics system 700A may still use robotic arms that are positioned outside of the sterile boundary and that are covered with sterilized drapes to perform a surgical procedure.

In one embodiment, the surgical robotics system 700A configures the set of robotic arms to perform an endoscopy surgical procedure on the patient 708. The set of robotic arms hold an endoscope, e.g., the surgical instrument 710. The set of robotic arms insert the endoscope into the patient's body via an opening in the groin area of the patient 708. The endoscope is a flexible, slender, and tubular instrument with optical components such as a camera and optical cable. The optical components collect data representing images of portions inside the patient's body. A user of the surgical robotics system 700A uses the data to assist with performing the endoscopy.

Figure 7B:
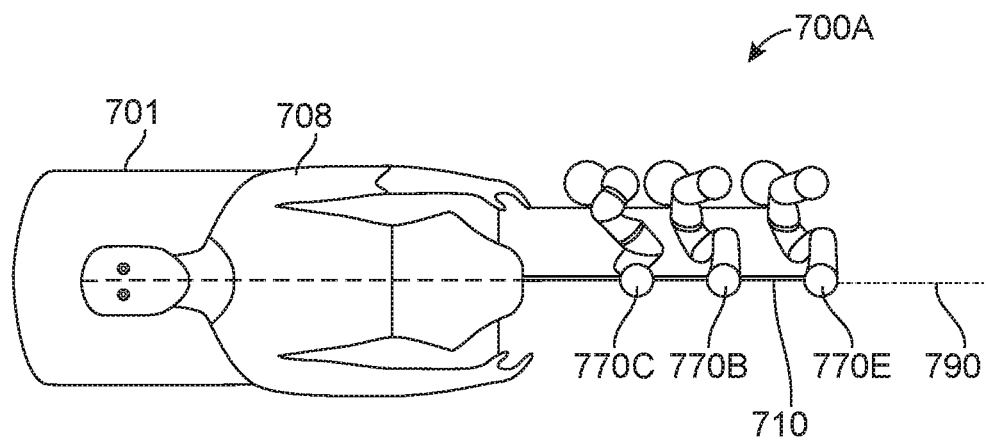
FIG. 7B is a top view of the surgical robotics system with column-mounted arms configured to access the lower body area of the patient according to one embodiment.

FIG. 7B is a top view of the surgical robotics system 700A with column-mounted arms configured to access the lower body area of the patient 708 according to one embodiment.

Figure 7C:
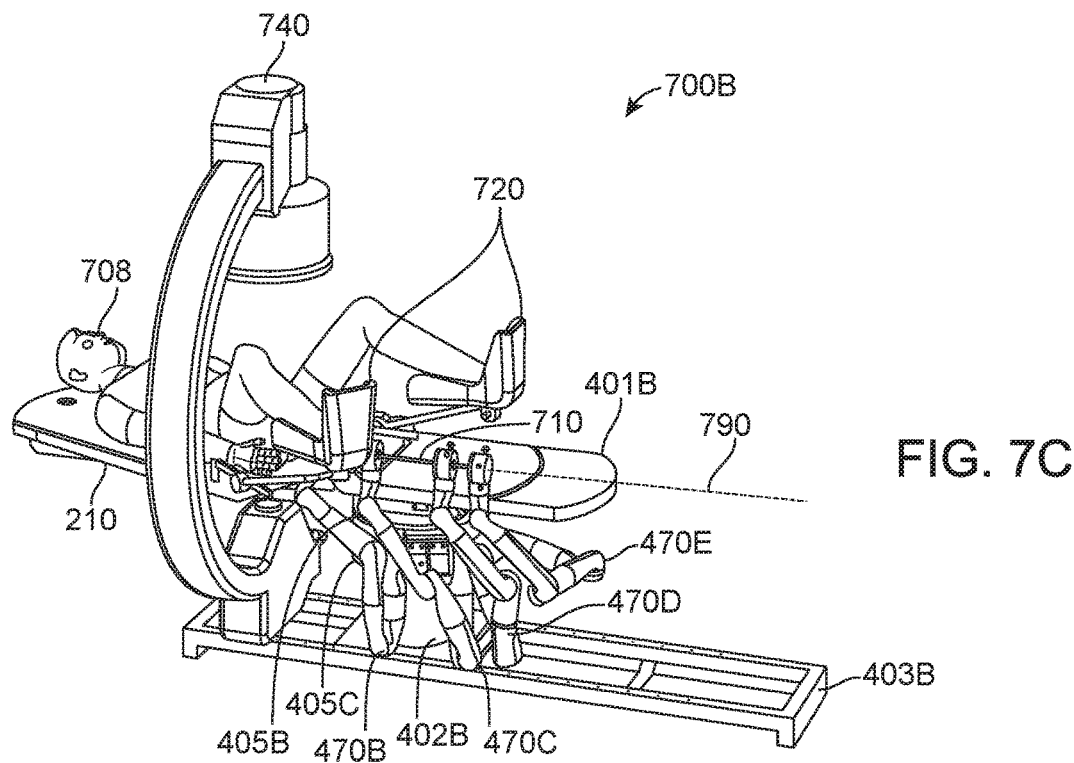
FIG. 7C is an isometric view of an imaging device and a surgical robotics system with column-mounted arms configured to access the lower body area of a patient according to one embodiment.

FIG. 7C is an isometric view of an imaging device 740 and a surgical robotics system 700B with column-mounted arms configured to access the lower body area of a patient 708 according to one embodiment. The surgical robotics system 700B is an embodiment of the surgical robotics system 400B in FIG. 4B. The surgical robotics system 700B includes a pair of stirrups 720 that support the legs of the patient 708, and thus exposing the groin area of the patient 708. Generally, the imaging device 740 captures images of body parts or other objects inside a patient 708. The imaging device 740 may be a C-arm, also referred to as a mobile C-arm, which is often used for fluoroscopy type surgical procedures, or another type of imaging device. A C-arm includes a generator, detector, and imaging system (not shown). The generator is coupled to the bottom end of the C-arm and faces upward toward the patient 708. The detector is coupled to the top end of the C-arm and faces downward toward the patient 708. The generator emits X-ray waves toward the patient 708. The X-ray waves penetrate the patient 708 and are received by the detector. Based on the received X-ray waves, the imaging system 740 generates the images of body parts or other objects inside the patient 708. The swivel segment 210 of the table 401B is rotated laterally such that the groin area of the patient 708 is aligned in between the generator and detector of the C-arm imaging device 740. The C-arm is a physically large device with a footprint that needs to stationed underneath the patient. In particular, the generator of the C-arm needs to be underneath the operative area of the patient, e.g., the abdomen area. In typical surgical beds mounted to a column, the column interferes with the positioning of the C-arm generator, e.g., because the column is also underneath the operative area. In contrast, due to the configurability of the swivel segment 210, the surgical robotics system 700B may configure the table 401B such that the C-arm, the robotic arms, and a user (e.g., physician) have a sufficient range of access to perform a surgical procedure on a working area the patient's body. In one example use case, the table 401B is translated laterally along a longitudinal axis of the table 401B such that the robotic arms can access the groin or lower abdomen area of a patient on the table 401B. In another example use case, by rotating the swivel segment 210 away from the column 402B, the generator of the C-arm 740 may be positioned underneath the groin area of the patient 708. The swivel segment 210—with a patient lying on the swivel segment 210—may be rotated at least to 45 degrees relative to a longitudinal axis of the table 401B without tipping over the surgical robotics system. In particular, the surgical robotics system does not tip because the center of mass of the surgical robotics system (e.g., the center of mass of the combined, at least, table, bed, and base) is positioned above a footprint of the base. Outrigger casters, further described with reference to FIGS. 8G-J in Section VIII. Base, may provide further stability to prevent the surgical robotics system from tipping over when a swivel segment is rotated away from the table.

The surgical robotics system 700B uses a set of column-mounted robotic arms to manipulate a surgical instrument 710. Each of the robotic arms is coupled to, e.g., holding, the surgical instrument 710. The surgical robotics system 700B uses the robotic arms to insert the surgical instrument 710 into the groin area of the patient along a virtual rail 790.

Figure 7D:
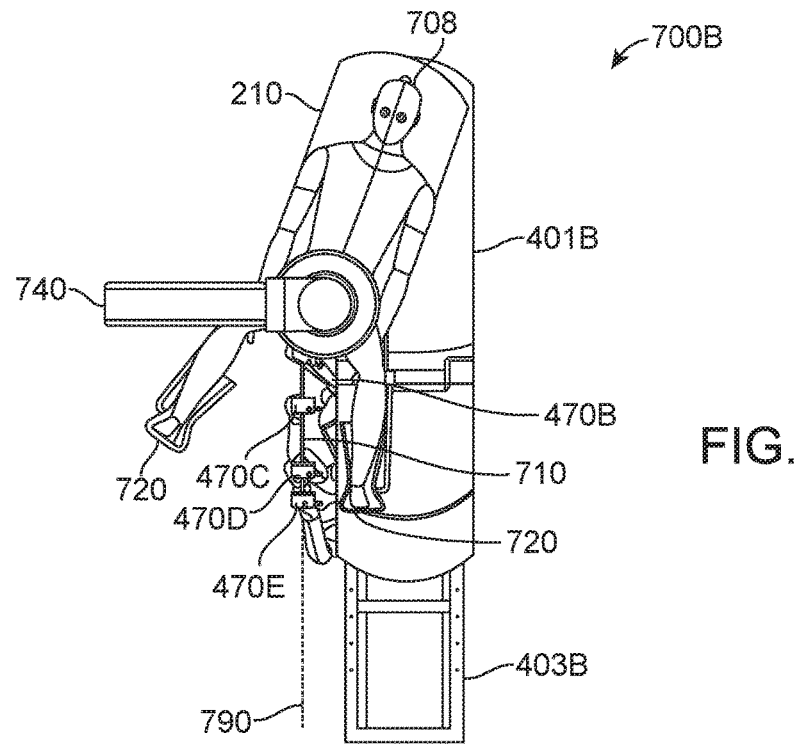
FIG. 7D is a top view of the imaging device and the surgical robotics system with column-mounted arms configured to access the lower body area of the patient according to one embodiment.

FIG. 7D is a top view of the imaging device 740 and the surgical robotics system 700B with column-mounted arms configured to access the lower body area of the patient 708 according to one embodiment.

VII. B. Core Body Surgery

Figure 7E:
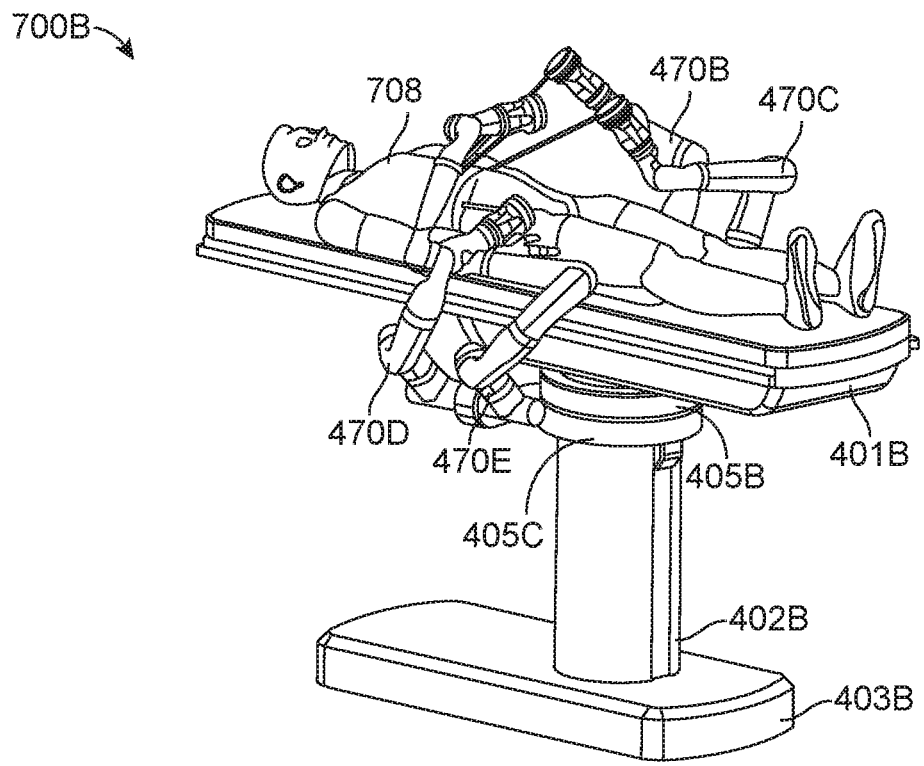
FIG. 7E is an isometric view of the surgical robotics system with column-mounted arms configured to access the core body area of a patient according to one embodiment.

FIG. 7E is an isometric view of the surgical robotics system 700B (or 400B) with column-mounted arms configured to access the core body area of a patient 708 according to one embodiment. The surgical robotics system 700B has been reconfigured from the configuration shown in FIG. 7C-D where the robotic arms access the lower body area of the patient 708. In embodiments where the table includes a swivel segment 210, the swivel segment 210 of the table is rotated in-line with the rest of the table. The patient 708 lying on the table 401B is undergoing a surgical procedure, e.g., prostatectomy or laparoscopy, requiring access to the core body area of the patient 708. Each robotic arm is manipulating a surgical instrument to perform the surgical procedure. The surgical robotics system 700B raises the column rings 405B and 405C toward the table 401B so that the robotic arms have greater access the patient 708. Further, the surgical robotics system 700B rotates the column rings such that two of the robotic arms extend from one side of the table 401B and the other two robotic arms extend from the opposite side of the 401B. Thus, the robotic arms are less likely to interfere with each other (e.g., a robotic arm blocking the motion of another robotic arm) during the surgical procedure.

VII. C. Upper Body Surgery

Figure 7F:
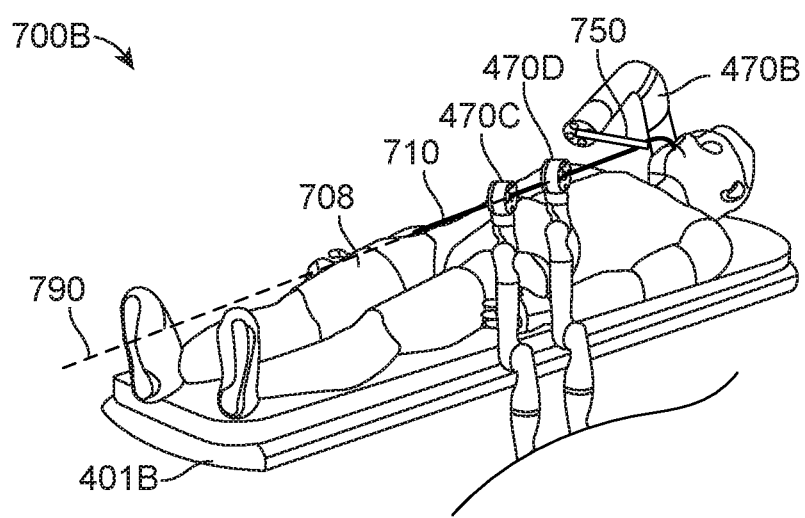
FIG. 7F is an isometric view of the surgical robotics system with column-mounted arms configured to access the upper body area of a patient according to one embodiment.

FIG. 7F is an isometric view of the surgical robotics system 700B (or 400B) with column-mounted arms configured to access the upper body area of a patient 708 according to one embodiment. The surgical robotics system 700B has been reconfigured from the configuration shown in FIG. 7E where the robotic arms access the core body area of the patient 708. In embodiments where the table includes a swivel segment 210, the swivel segment 210 of the table is rotated in-line with the rest of the table. The patient 708 lying on the table 401B is undergoing a surgical procedure, e.g., bronchoscopy, requiring access to the upper body area of the patient 708, specifically the head of the patient 708. The robotic arm 470C and the robotic arm 470D are inserting a surgical instrument 710D, e.g., a bronchoscope, into the mouth of the patient 708 along a virtual rail 790. The robotic arm 470B is coupled to, e.g., holding, an introducer 750. The introducer 750 is a surgical instrument that directs the bronchoscope into the mouth of the patient 708. Specifically, the trajectory of the bronchoscope along the virtual rail 790 begins parallel to the patient 708. The introducer 750 changes the angle of the virtual rail 790 just before the bronchoscope enters the mouth. The robotic arm 470E (not shown in FIG. 7F) is not used for the surgical procedure, and thus is stowed away.

VIII. Base

Figure 8A:
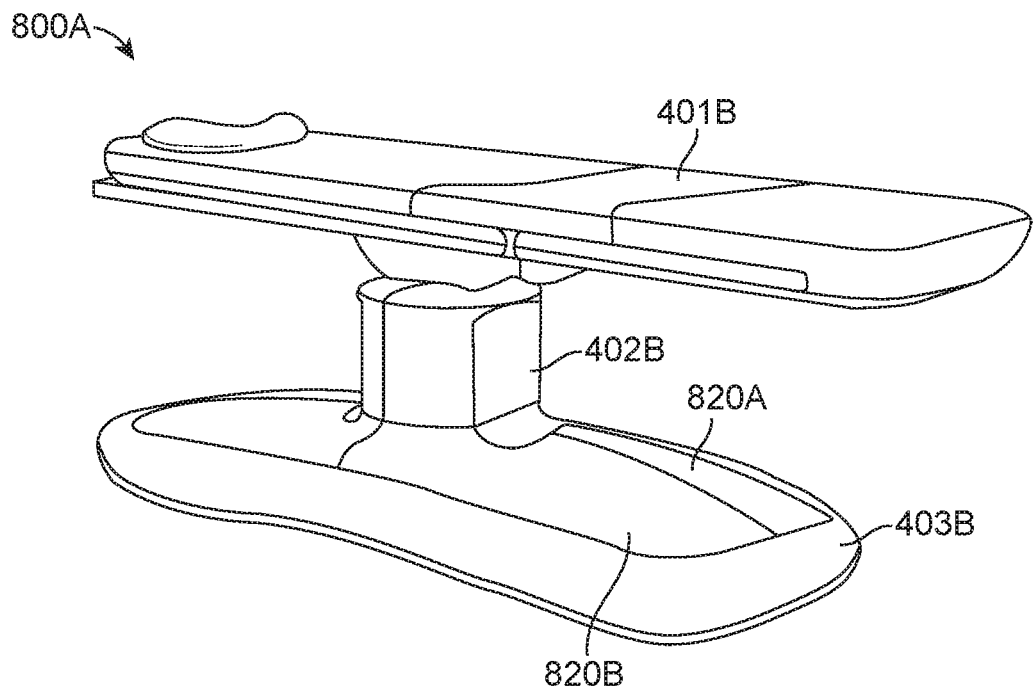
FIG. 8A is an isometric view of a base of a surgical robotics system according to one embodiment.

FIG. 8A is an isometric view of a base 403A of a surgical robotics system 800A according to one embodiment. The surgical robotics system 800A is an embodiment of the surgical robotics system 400B in FIG. 4B. The surgical robotics system 800A stores column-mounted robotic arms and/or column rings (not shown) inside the base 403B when the robotic arms are not in use. The base 403B includes a first panel 820A and a second panel 820B that cover stored robotic arms. The first panel 820A and the second panel 820B are advantageous because they prevent waste materials from de-sterilizing or otherwise contaminating stored robotic arms.

Figure 8B:
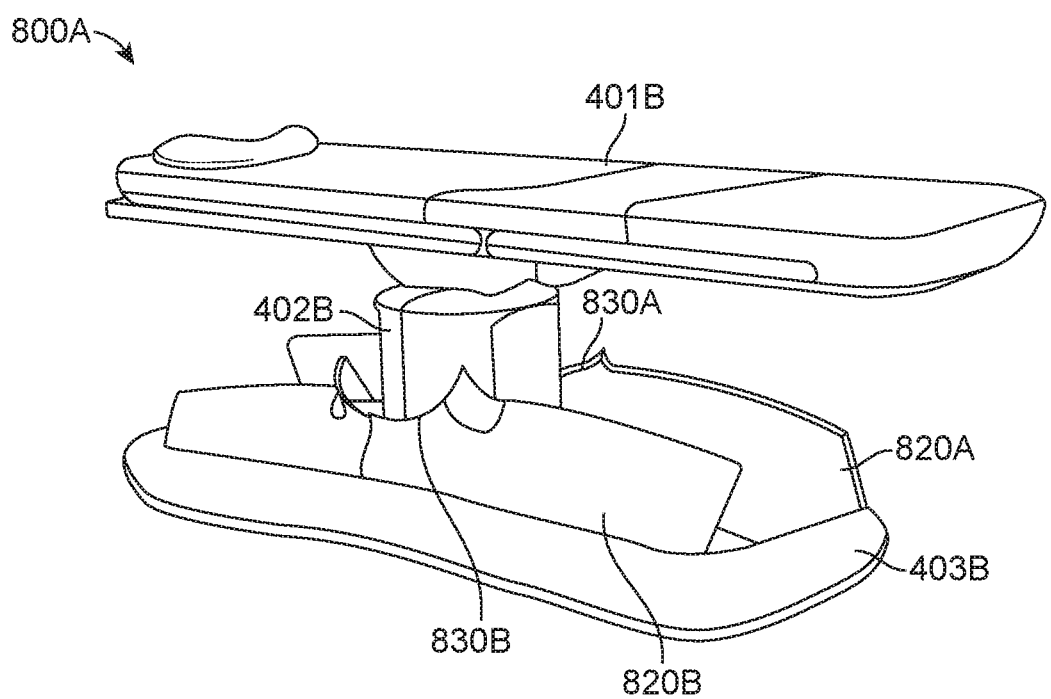
FIG. 8B is an isometric view of open panels of the base according to one embodiment.

FIG. 8B is an isometric view of open panels of the base 403B according to one embodiment. The first panel 820A and the second panel 820B pivot away from the column 802A such that column-mounted robotic arms have access to inside the base 403B. The first panel 820A includes a cutout 830A and the second panel 820B includes a cutout 830B. The cutouts 830A and 830B conform to the shape of the column 402B such that the panels 820A and 820B form a seal around the column 402B when closed. The surgical robotics system 800A may automatically open and close the first panel 820A and the second panel 820B using motors or other means of actuation. A user of the surgical robotics system 800A may also manually open and close the first panel 820A and the second panel 820B.

Figure 8C:
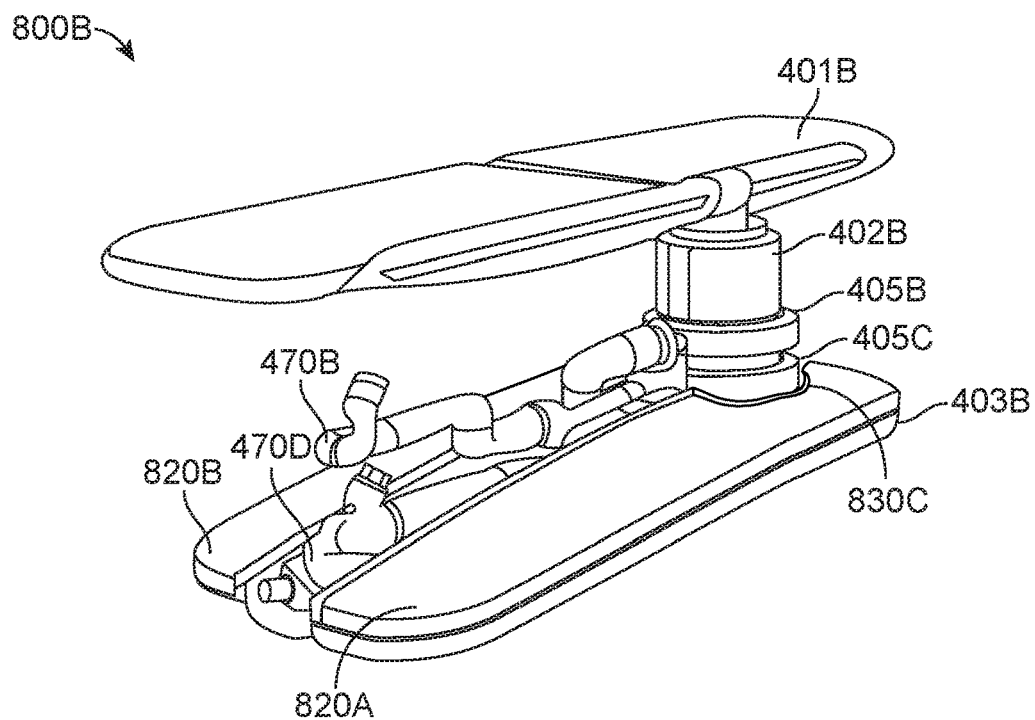
FIG. 8C is an isometric view of robotic arms stowed inside a base of a surgical robotics system according to one embodiment.

FIG. 8C is an isometric view of a robotic arm stowed inside a base 403B of a surgical robotics system 800B according to one embodiment. The surgical robotics system 800B is an embodiment of the surgical robotics system 400B in FIG. 4B. The surgical robotics system 800B stores column-mounted robotic arms 470B and 470D and column rings 405B and 405C inside the base 403B when the robotic arms are not in use. The base 403B includes a first panel 820A and a second panel 820B that cover stored robotic arms and column rings. The first panel 820A includes a cutout 830C. The second panel 820B also includes a cutout (not shown due to being obscured by other components).

The cutouts conform to the shape of the column 402B such that the panels 820A and 820B form a seal around the column 402B when closed.

The first panel 820A and a second panel 820B translate laterally to provide access for the robotic arms and column rings into the base 403B. FIG. 8C shows the first panel 820A and a second panel 820B translated to form an opening. The opening may be large enough to provide access for a robotic arm, but not too large as to still provide protection to the robotic arms even when the panels are open. The robotic arm 470D and column ring 405C are stowed inside the base 403B. The robotic arm 470B and column ring 405B are outside the base 403B, though they may also be stowed inside the base 403B. The surgical robotics system 800B may automatically open and close the first panel 820A and the second panel 820B using motors or other means of actuation. A user of the surgical robotics system 800B may also manually open and close the first panel 820A and the second panel 820B.

Figure 8D:
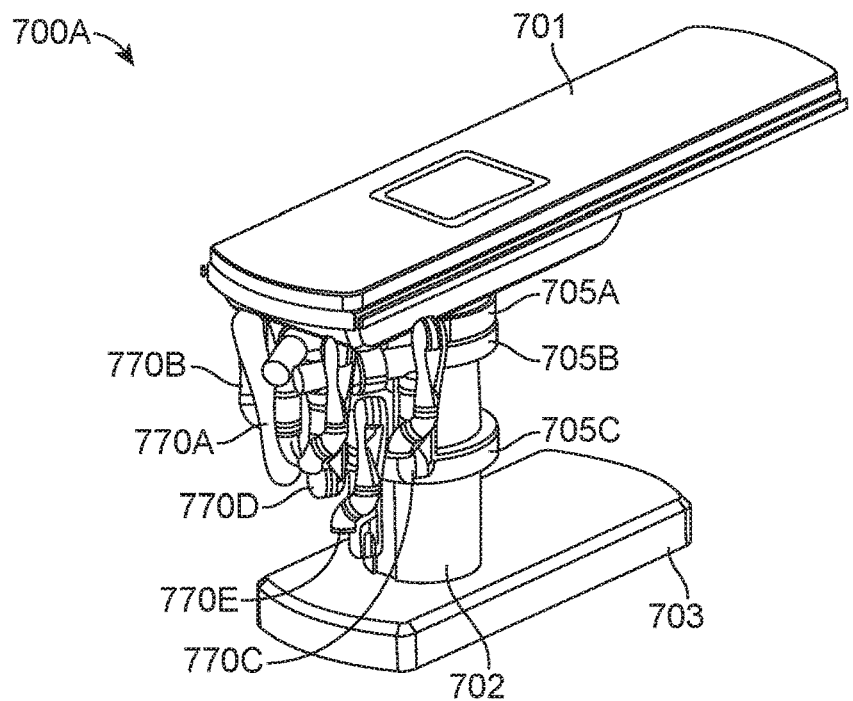
FIG. 8D is an isometric view of robotic arms stowed underneath a table of a surgical robotics system according to one embodiment.

FIG. 8D is an isometric view of robotic arms stowed underneath the table 701 of the surgical robotics system 700A according to one embodiment. Specifically, the arm segments of each robotic arm rotate such that the robotic arm is in a compact configuration for stowage. The surgical robotics system 700A raises the first column ring 705A and the second column ring 705B, and lowers the third column ring 705C toward the center of the column 702. This way, the robotic arms have enough space in the stowed configuration without interfering with each other. In one embodiment, the column 702 includes covers (e.g., similar to panels 820A and 820B) over the robotics arms to protect the robotic arms from contamination or damage.

Figure 8E:
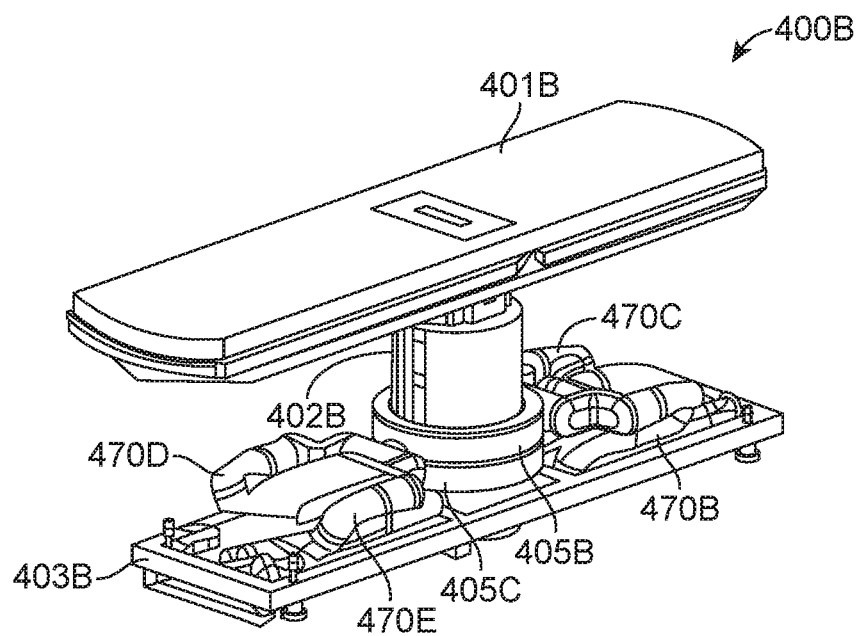
FIG. 8E is an isometric view of robotic arms stowed above a base of a surgical robotics system according to one embodiment.

FIG. 8E is an isometric view of robotic arms stowed above the base 403B of the surgical robotics system 400B according to one embodiment. The robotic arms 470B, 470C, 470D, and 470E are in a stowed configuration. Specifically, the arm segments of each robotic arm rotate such that the robotic arm is in a compact configuration for stowage. The surgical robotics system 400B lowers the first column ring 405B and the second column ring 405C along the column 402B such that the stowed robotic arms rest on the base 403B and are away from the table 401B. A cover (not shown) such as a drape or panel may be used to cover the stowed robotic arms for protection from de-sterilization or other contamination.

Figure 8F:
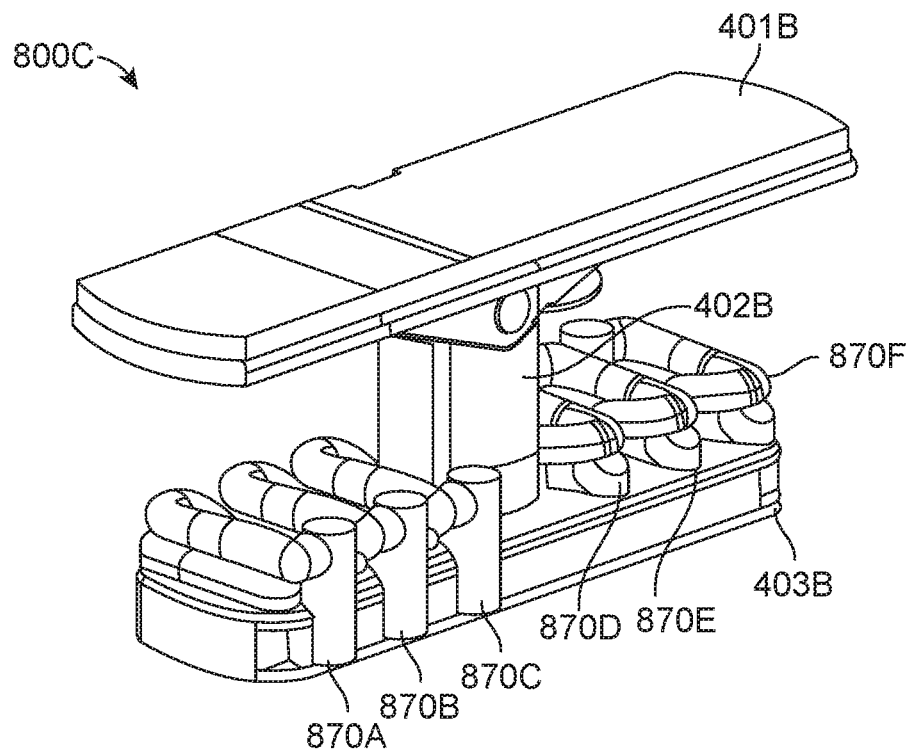
FIG. 8F is another isometric view of robotic arms stowed above a base of a surgical robotics system according to one embodiment.

FIG. 8F is another isometric view of robotic arms stowed above the base 403B of the surgical robotics system 800C according to one embodiment. The robotic arms are rail-mounted instead of column-mounted. Rail-mounted robotic arms are further described with reference to FIGS. 9A-B and FIGS. 10A-D in Section IX. Rail-Mounted Robotic Arms and Section X. Rails, respectively. The surgical robotics system 800C is an embodiment of the surgical robotics system 900B further described with reference to FIG. 9B in Section IX. Rail-Mounted Robotic Arms. The robotic arms 870C, 870D, 870E, 870F, 870G, and 870H are in a stowed configuration.

Figure 8G:
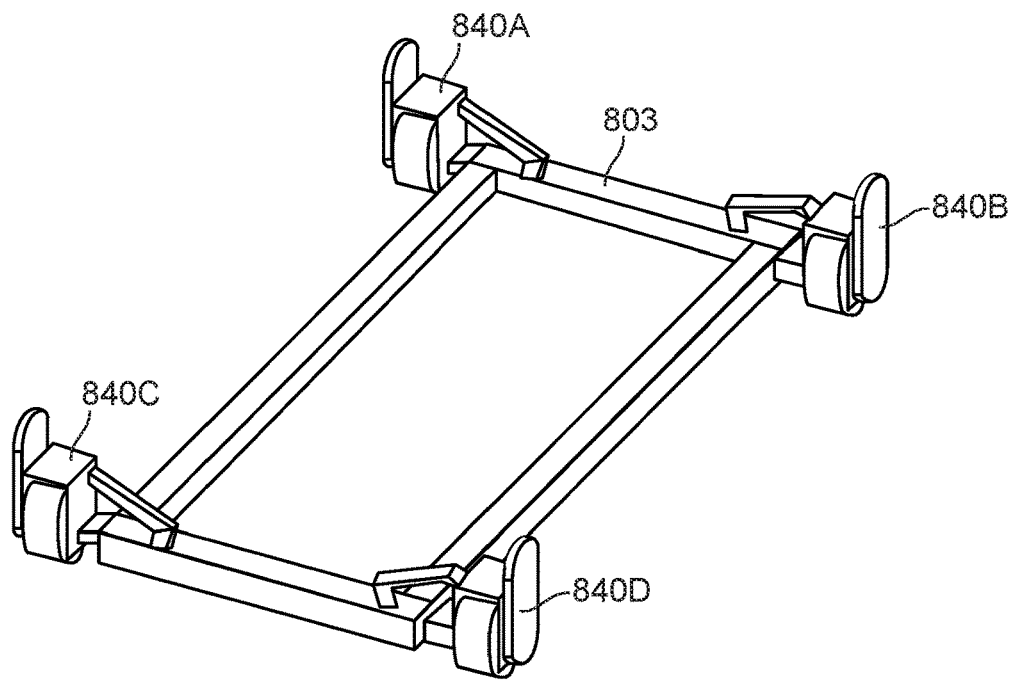
FIG. 8G is an isometric view of outrigger casters on a base of a surgical robotics system according to one embodiment.

FIG. 8G is an isometric view of outrigger casters on a base 803 of a surgical robotics system according to one embodiment. The base 803 shown in FIG. 8G includes four outrigger casters 840A, 840B, 840C, and 840D, each substantially the same as each other and positioned at a different corner of the base 803, though it should be noted that, in other embodiments, a base may include any number of outrigger casters positioned in other locations on the base. The outrigger casters 840A, 840B, 840C, and 840D are each in a mobile configuration, i.e., the caster wheel physically contacts the ground. Thus, a user of the surgical robotics system may transport the surgical robotics system using the caster wheels, e.g., to a storage area when the surgical robotics system is not in use.

Figure 8H:
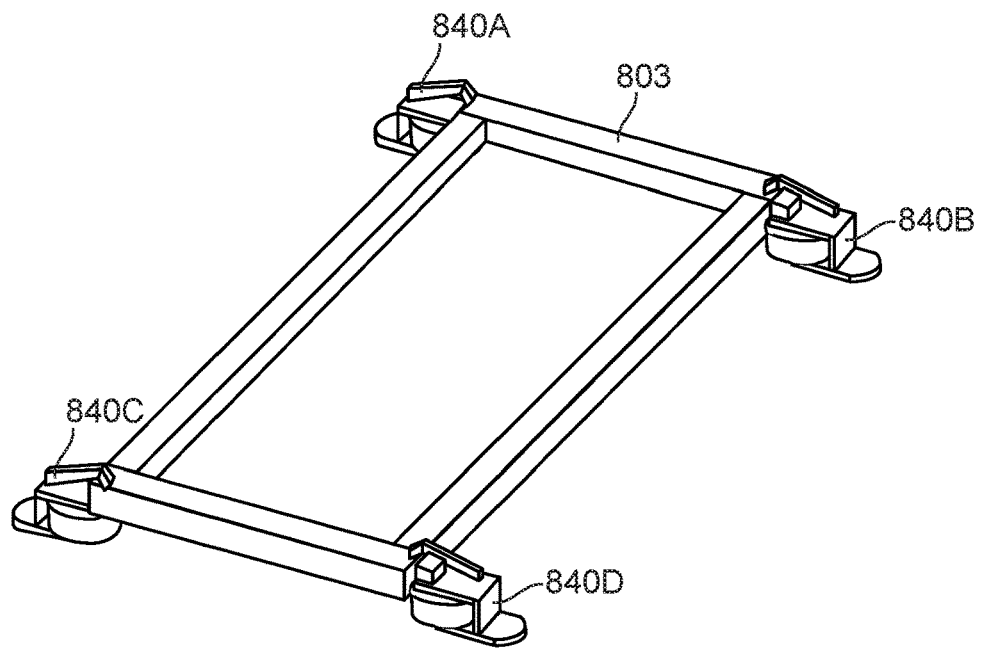
FIG. 8H is another isometric view of the outrigger casters on the base of the surgical robotics system according to one embodiment.

FIG. 8H is another isometric view of the outrigger casters 840A, 840B, 840C, and 840D on the base 803 of the surgical robotics system according to one embodiment. The outrigger casters 840A, 840B, 840C, and 840D are each in a stationary configuration, i.e., the outrigger caster is rotated such that the caster wheel does not physically contact the ground. Thus, the surgical robotics system may be stabilized and immobilized during a surgical procedure.

Figure 8I:
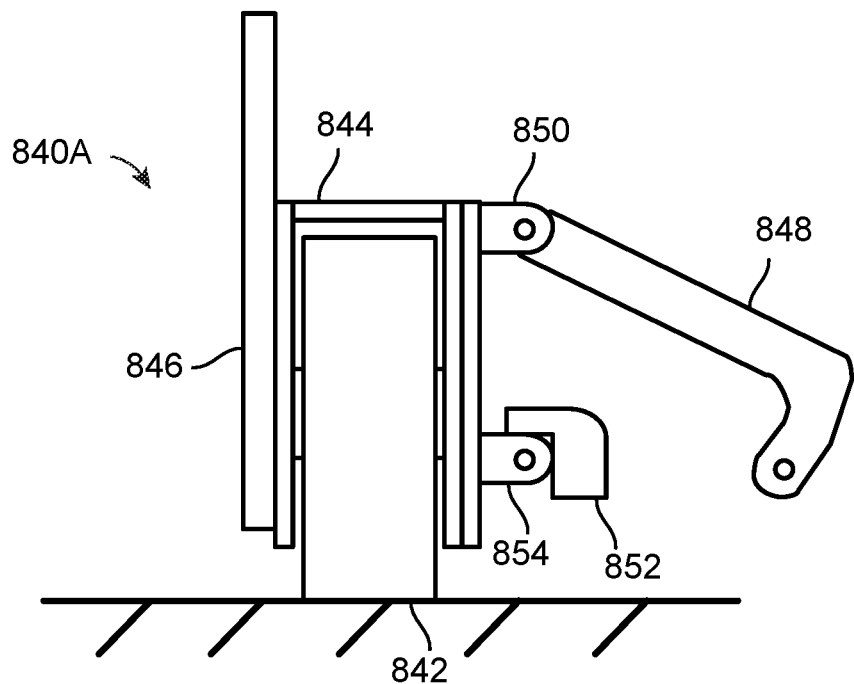
FIG. 8I is a side view of an outrigger caster in a mobile configuration according to one embodiment.

FIG. 8I is a side view of the outrigger caster 840A in a mobile configuration according to one embodiment. The outrigger caster 840A includes a caster wheel 842 movably coupled to an outrigger mount 844. The outrigger mount 844 is coupled to a foot 846. The first linkage 848 is movably coupled to the outrigger mount 844 by the first hinge 850. The second linkage 852 is movably coupled to the outrigger mount 844 by the second hinge 854. In the mobile configuration, the caster wheel 842 may rotate to move the outrigger caster 840 along the ground.

Figure 8J:
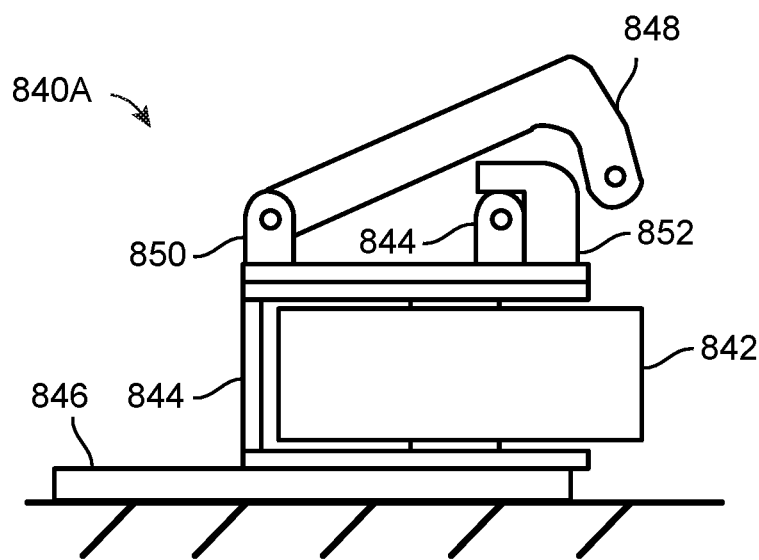
FIG. 8J is a side view of the outrigger caster in a stationary configuration according to one embodiment.

FIG. 8J is a side view of the outrigger caster 840A in a stationary configuration according to one embodiment. In the stationary configuration, the caster wheel 842 may freely rotate, but the caster wheel 842 does not move the outrigger caster 840A because the caster wheel 842 is not physically in contact with the ground. The surgical robotics system (or a user) rotates the outrigger caster 840A, e.g., 90 degrees, to change the outrigger caster 840A from the mobile configuration to the stationary configuration. Thus, the foot 846 now physically contacts the ground, and helps prevent the surgical robotics system from moving. The foot 846 may have a larger footprint relative to the caster wheel 842 to provide additional stability on the ground. The linkages 848 and 852 are positioned such that they do not interfere with the rotational path of the outrigger caster 840A. Combining the caster wheel 842 and the foot 846 in the outrigger caster 840A is advantageous, e.g., because the outrigger caster 840A allows the surgical robotics system to change between the mobile and stationary configurations using a compact mechanism, compared to having separate mechanisms for casters and stabilization. Further, in use cases of surgical robotics systems including swivel segments that rotate a patient lying on the swivel segment away from a corresponding table (e.g., as illustrated in FIGS. 7C-D), the feet of outrigger casters (in the stationary configuration) help prevent the surgical robotics system from tipping over due to the center of mass of the patient extending beyond the table base.

Alternative views and embodiments of the base 403B including the above mentioned components are further illustrated and described at least in U.S. Provisional Application No. 62/203,530 filed Aug. 11, 2015.

IX. Rail-Mounted Robotic Arms

Figure 9A:
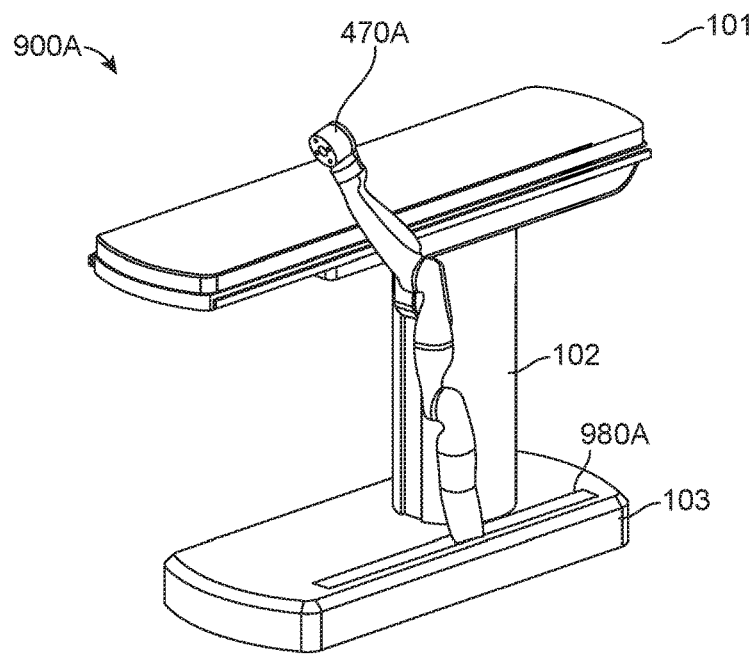
FIG. 9A is an isometric view of a surgical robotics system with a rail-mounted robotic arm according to one embodiment.

FIG. 9A is an isometric view of a surgical robotics system 900A with a rail-mounted robotic arm according to one embodiment. The surgical robotics system 900A includes a set of robotic arms (including at least arm 470A) and a set of base rails (including at least base rail 980A). The robotic arm 470A is coupled to the base rail 980A. Base rails are further described with respect to FIGS. 10A-D in Section X. Rails below. The base rail 980A is movably coupled to the base 103. Thus, the robotic arm 470A may be referred to as a rail-mounted robotic arm 470A.

Figure 9B:
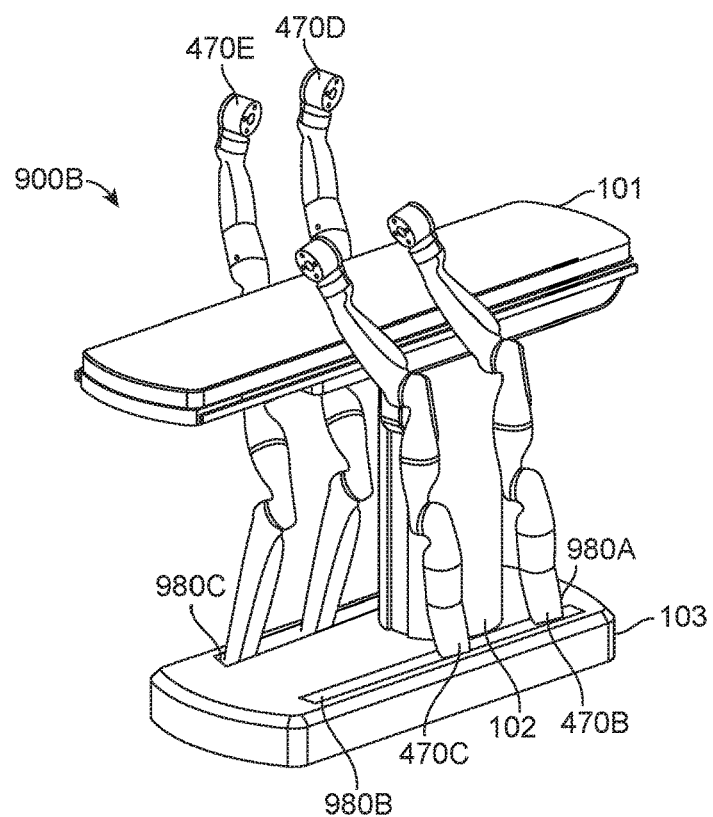
FIG. 9B is an isometric view of a surgical robotics system with rail-mounted robotic arms according to one embodiment.

FIG. 9B is an isometric view of a surgical robotics system 900B with rail-mounted robotic arms according to one embodiment. The surgical robotics system 900B includes robotic arms 470B, 470C, 470D, and 470E each coupled to a first base rail 980B or a second base rail 980C. The first base rail 980B and the second base rail 980C are movably coupled to the base 103.

In other embodiments, the surgical robotics system 900B may include additional or fewer robotic arms and/or base rails. Further, the robotic arms may be coupled to base rails in various configurations. For example, three robotic arms may be coupled to a base rail. Additionally, the surgical robotics system 900B may include three base rails each coupled to a robotic arm.

The surgical robotics system 900B may translate robotic arms mounted to a base rail by translating the base rails relative to the base 103. Base rails may translate beyond the starting footprint of the base 103, which allows the robotic arms to operate in a larger volume of space. Further, the surgical robotics system 900B may translate robotic arms mounted to a base rail independently from each other by translating the robotic arms relative to the base rail. This is advantageous, for example, because the surgical robotics system 900B may position the robotic arms in different configurations to perform a variety of surgical procedures.

Alternative views and embodiments of the surgical robotics system 900B with rail-mounted robotic arms including the above mentioned components are further illustrated and described at least in U.S. Provisional Application No. 62/193,604 filed Jul. 17, 2015 and U.S. Provisional Application No. 62/201,518 filed Aug. 5, 2015.

X. Rails

Figure 10A:
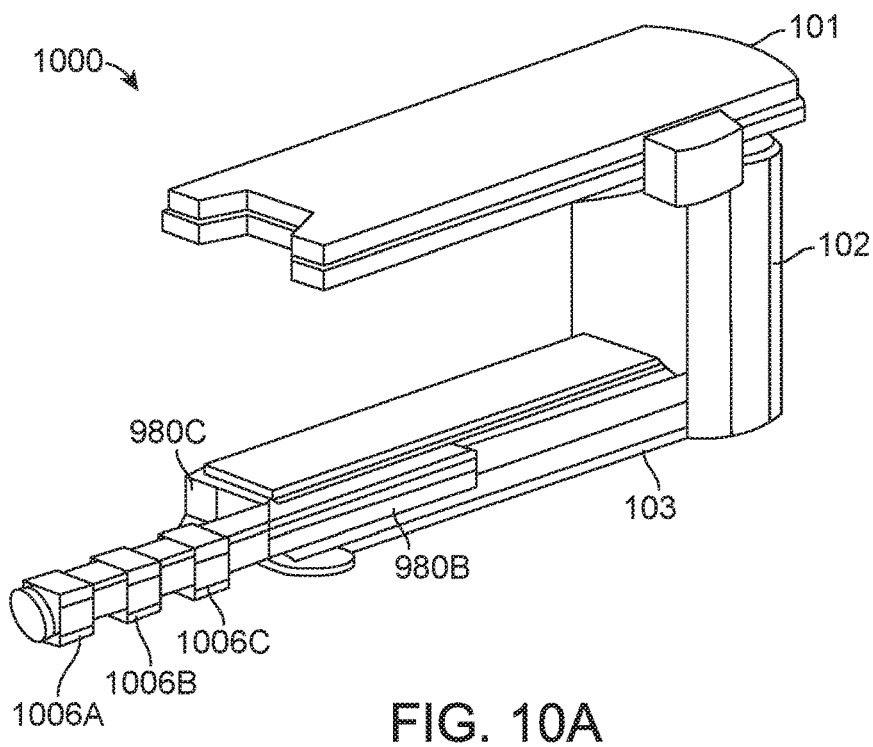
FIG. 10A is an isometric view of base rails of a surgical robotics system according to one embodiment.

FIG. 10A is an isometric view of base rails of a surgical robotics system 1000 according to one embodiment. A base rail includes a set of one or more arm mounts each movably coupled to the base rail. Further, each arm mount is an embodiment of the arm mount 506A or 506B previously described with reference to FIG. 5A in Section V. Column Ring. Specifically, the base rail 980B includes arm mounts 1006A, 1006B, and 1006C.

Figure 10B:
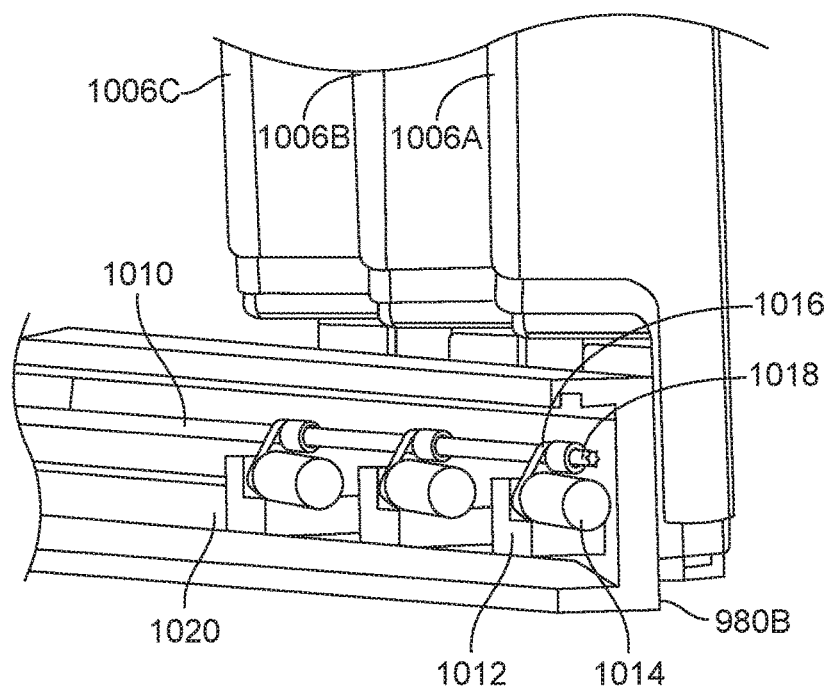
FIG. 10B is an isometric view of arm mounts on the base rail according to one embodiment.

FIG. 10B is an isometric view of arm mounts on the base rail 980B according to one embodiment. The arm mounts 1006A, 1006B, and 1006C each include a belt and pinion assembly. Specifically, the belt and pinion assembly of arm mount 1006A includes a bracket 1012, motor 1014, belt 1016, and pinion 1018. The belt and pinion assemblies of arm mount 1006B and 1006C are constructed similarly.

The surgical robotics system 1000 translates arm mounts—and thus, robotic arms mounted to the arm mounts—along base rails using the belt and pinion assemblies. Specifically, the arm mount 1006A is movably coupled to a channel 1020 of the base rail 980B by the bracket 1012. The bracket 1012 is coupled to motor 1014, belt 1016, and pinion 1018. The motor 1014 is coupled to the pinion 1018 by the belt 1016. Thus, output rotation of the motor 1014 causes the pinion 1018 to rotate. The pinion 1018 is engaged with a rail lead screw 1010 of the base rail 980B. Rotation of the pinion 1018 causes the arm mount 1006A to translate along the base rail 980B parallel to the rail lead screw 1010.

Figure 10C:
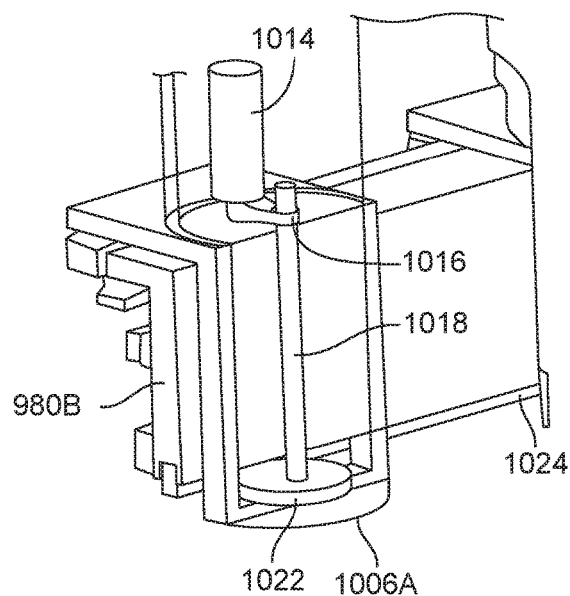
FIG. 10C is an isometric cutaway view of an arm mount on the base rail according to one embodiment.

FIG. 10C is an isometric cutaway view of an arm mount 1006A on the base rail 980B according to one embodiment. The arm mount 1006A includes a belt and pinion assembly. Specifically, the belt and pinion assembly includes a motor 1014, belt 1016, pinion 1018, and bearing 1022. The surgical robotics system 1000 translates the arm mount 1006A—and thus, a robotic arm mounted to the arm mount 1006A—along the base rail 980B using the belt and pinion assembly. The motor 1014 is coupled to the pinion 1018 by the belt 1016. Thus, output rotation of the motor 1014 causes the pinion 1018 to rotate. The pinion 1018 is coupled to the bearing 1022. In some embodiments, the bearing 1022 forms a rack and pinion assembly with the base rail 980B. Specifically, the bearing 1022 is a gear (i.e., the pinion) and is engaged with a rack 1024 of the base rail 980B. Rotation of the pinion 1018 causes the bearing 1022 to translate along the base rail 980B parallel to the rack 1024. Thus, the arm mount 1006A also translates along the base rail 980B.

Figure 10D:
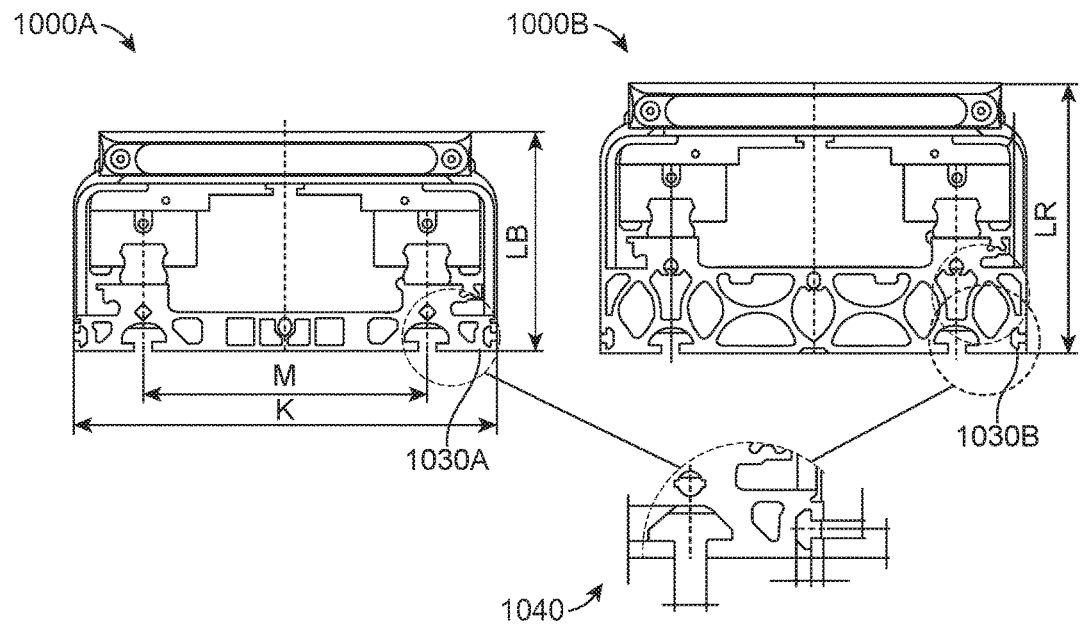
FIG. 10D is cross sectional views of the base rail according to one embodiment.

FIG. 10D is cross sectional views of the base rail 980B according to one embodiment. The cross sectional view 1000A shows a basic profile of an embodiment of the base rail 980B. The cross sectional view 1000B shows a reinforced profile of an embodiment of the base rail 980B. The lower segment 1030B of the reinforced profile is larger in size than the lower segment 1030A of the basic profile. Thus, the reinforced profile is an advantage, for example, because it enables the base rail 980B to withstand greater loads relative to the basic profile. Both the basic and the reinforced profiles have a T-slot attachment 1040, which engages with a corresponding T-slot on a base of a surgical robotics system.

Alternative views and embodiments of the base rails 980A, 980B, and 980C including the above mentioned components are further illustrated and described at least in U.S. Provisional Application No. 62/193,604 filed Jul. 17, 2015 and U.S. Provisional Application No. 62/201,518 filed Aug. 5, 2015.

XI. Alternate Configurations

XI. A. Hybrid Configuration

Figure 11:
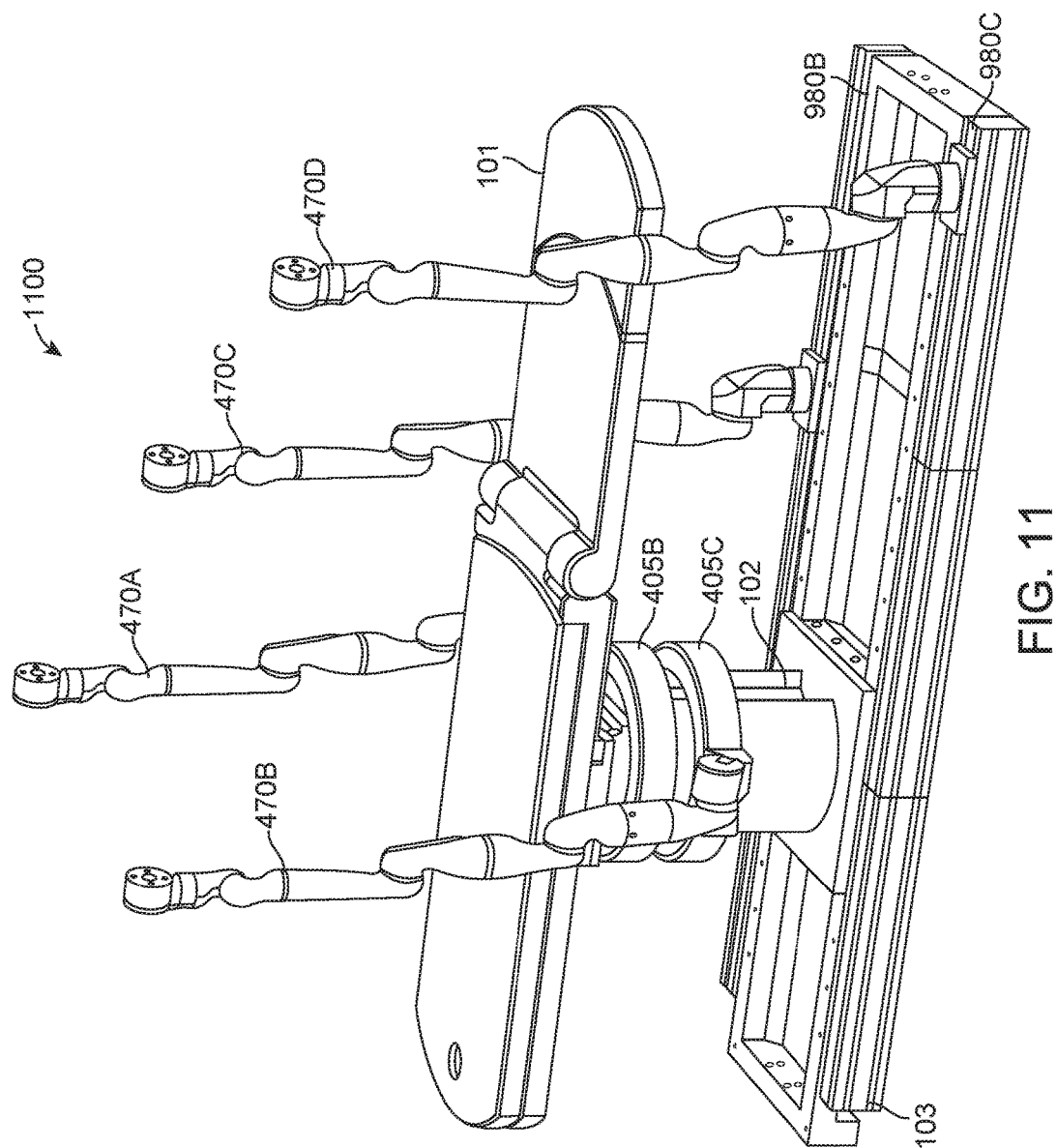
FIG. 11 is an isometric view of a surgical robotics system with column-mounted robotics arms and rail-mounted robotic arms according to one embodiment.

FIG. 11 is an isometric view of a surgical robotics system 1100 with column-mounted robotics arms and rail-mounted robotic arms according to one embodiment. Due to the hybrid configuration including both column-mounted robotics arms and rail-mounted robotic arms, the surgical robotics system 1100 may configure the robotic arms in a greater number of (or different types of) positions compared to surgical robotics systems with column-mounted robotics arms only or rail-mounted robotic arms only. Further, the surgical robotics system 1100 takes advantage of the rotational motion of robotic arms using the column rings as well as translational motion of the robotic arms using the base rails.

XI. B. Cart-Based Robotic Arm Column

Figure 12:
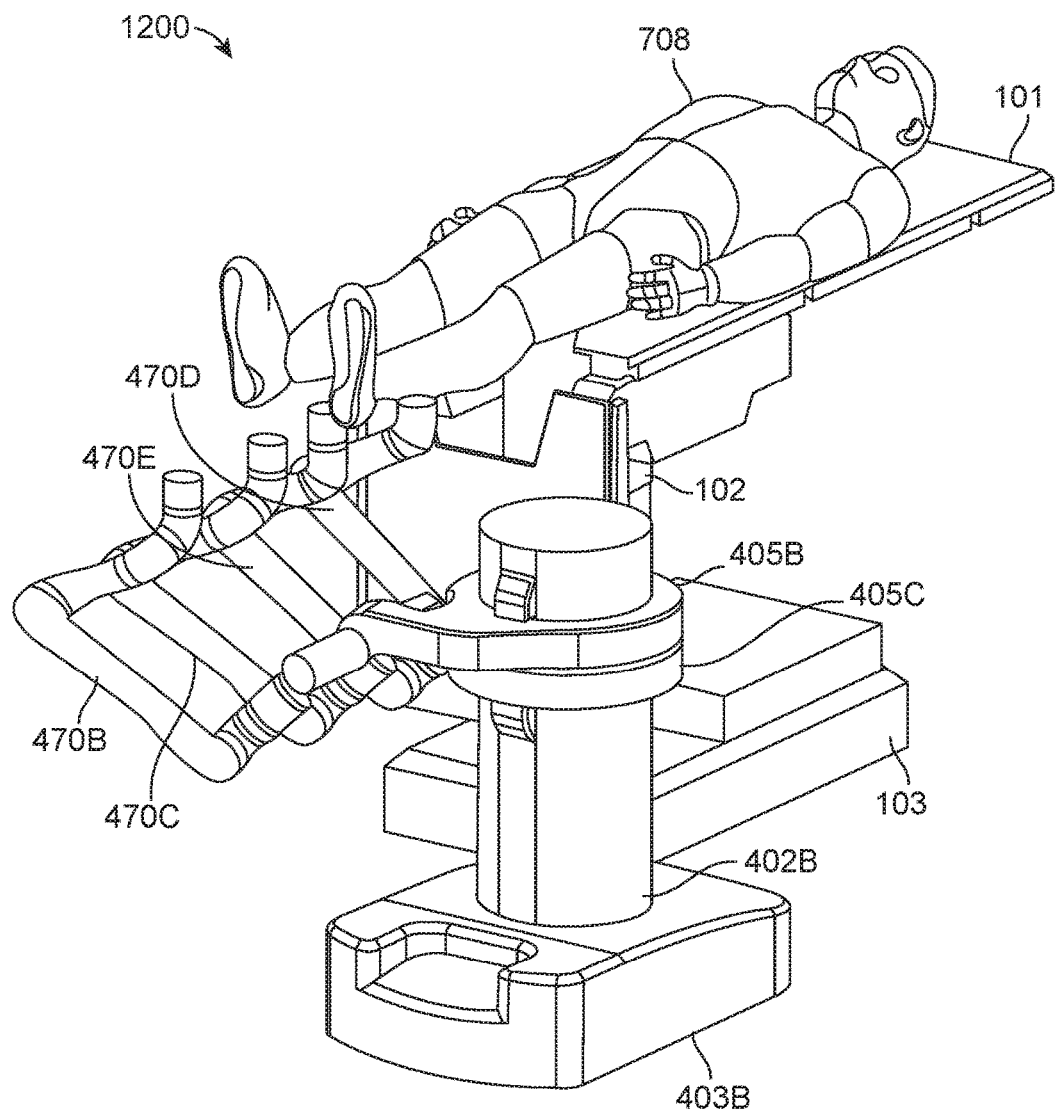
FIG. 12 is an isometric view of a surgical robotics system with column-mounted robotics arms on a platform separate from a table and a base of the surgical robotics system according to one embodiment.

FIG. 12 is an isometric view of a surgical robotics system 1200 with column-mounted robotics arms on a column 402B and base 403B separate, e.g., as a free standing cart, from a table 101, column 102, and base 103 of the surgical robotics system 1200 according to one embodiment. The surgical robotics system 1200 configures the robotic arms to access the lower body area of patient 708 lying on the table 101. In one embodiment, mounting the robotic arms on a cart including the column 402B separate from the column 102 coupled to the table 101 with the patient is advantageous. For example, because the surgical robotics system 1200 may configure the robotic arms to a greater number of (or different types of) positions compared to surgical robotics systems with robotics arms mounted to the same column as the table, which are limited at least in the angles where the table extends past the column 102. Further, the cart may include outrigger casters (e.g., previously described with reference to FIGS. 8G-J in Section VIII. Base) that allow users to more easily transport the robotic arms or keep the cart stationary. Mounting the robotic arms separately can also reduce the number of components and complexity of the column coupled to the table with the patient.

Alternative views and embodiments of the surgical robotics system 1100, the surgical robotics system 1200, and other surgical robotics systems including the above mentioned components are further illustrated and described at least in U.S. Provisional Application No. 62/162,486 filed May 15, 2015, U.S. Provisional Application No. 62/162,467 filed May 15, 2015, U.S. Provisional Application No. 62/193,604 filed Jul. 17, 2015, U.S. Provisional Application No. 62/201,518 filed Aug. 5, 2015, U.S. Provisional Application No. 62/203,530 filed Aug. 11, 2015, and U.S. Provisional Application No. 62/235,394 filed Sep. 30, 2015.

XII. Additional Considerations

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context unless otherwise explicitly stated.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

What is claimed is:

1. A system comprising:
   a table for supporting a patient positioned on the table;
   a column coupled to the table;
   a base coupled to the column;
   a column ring coupled to the column and configured to linearly translate relative to the table; and
   a robotic arm coupled to the base and configured to manipulate a medical instrument relative to the patient positioned on the table, wherein the robotic arm is further configured to be stowable within a volume of the base.

2. The system of claim 1, wherein the column ring is further configured to rotate around the column.

3. The system of claim 1, wherein the table comprises a table portion that is configured to be rotatable about a pivot.

4. The system of claim 1, wherein the table comprises a rail that is configured to translate relative to the column.

5. The system of claim 1, wherein the column ring further comprises an arm mount configured to position the robotic arm.

6. The system of claim 1, further comprising an angle rotation mechanism configured to change an angle of the table relative to the column.

7. The system of claim 6, wherein the angle rotation mechanism is configured to change the angle of the table relative to the column in at least two degrees of freedom.

8. The system of claim 1, wherein the column is cylindrical.

9. The system of claim 1, wherein the column ring is circular.

10. The system of claim 1, wherein the medical instrument comprises at least one of a catheter, an endoscope, and a laparoscope.

11. The system of claim 1, wherein the base comprises a panel configured to cover the volume in the base.

12. The system of claim 11, wherein the panel of the base is mechanically actuated.

13. The system of claim 11, wherein the panel is configured to translate laterally in order to allow the robotic arm to be stowed within the volume.

14. The system of claim 11, wherein the volume is sized to stow the column ring.

15. The system of claim 14, wherein the column ring is configured to translate into the volume in the base for stowage of the column ring.

16. A method comprising:
   positioning a patient on a table, the table coupled to a column and a base;
   translating a column ring along the column, the column ring coupled to the column and comprising an arm mount;
   positioning a robotic arm relative to the patient, the robotic arm coupled to the arm mount; and
   directing a medical instrument towards a location within the patient, the medical instrument coupled to the robotic arm.

17. The method of claim 16, the method further comprising rotating the column ring around the column.

18. The method of claim 16, the method further comprising changing an angle of the table relative to the column, wherein the table comprises an angle rotation mechanism configured to change the angle of the table relative to the column.

19. The method of claim 18, wherein changing the angle of the table comprises changing the angle in two degrees of freedom.

20. The method of claim 16, the method further comprising translating a panel in the base, the panel being configured to cover a volume of the base, and the volume being configured to stow the robotic arm and the column ring.

21. The method of claim 20, wherein the translating of the column ring comprises vertically translating the column ring from the volume in the base.

22. The method of claim 16, the method further comprising rotating a portion of the table about a pivot.

23. The method of claim 16, the method further comprising translating the table relative to the column.

24. The method of claim 16, wherein the positioning of the robotic arm comprises moving the arm mount to position the robotic arm proximate to the patient.

25. The method of claim 24, wherein the moving of the arm mount comprises rotating the arm mount along an arm mount axis.

26. The method of claim 16, wherein the directing of the medical instrument comprises directing the medical instrument through at least one of a small incision and a natural orifice.

27. The method of claim 26, wherein the medical instrument comprises at least one of a catheter, an endoscope, and a laparoscope.

28. The method of claim 16, wherein the translating the column ring, the positioning of the robotic arm, and the directing of the medical instrument are performed with minimal user intervention.

29. The method of claim 16, wherein the column ring is circular.

30. The method of claim 16, wherein the column is cylindrical.

* * * * *